(12) United States Patent
Zirps et al.

(10) Patent No.: US 9,782,564 B2
(45) Date of Patent: Oct. 10, 2017

(54) WHEEL FOR ROBOTIC CATHETER SYSTEM DRIVE MECHANISM

(71) Applicant: Corindus, Inc., Waltham, MA (US)

(72) Inventors: Christopher Zirps, Sharon, MA (US);
Tal Wenderow, Newton, MA (US);
John Murphy, North Reading, MA (US)

(73) Assignee: Corindus, Inc., Waltham, MA (US)

( * ) Notice: Subject to any disclaimer, the term of this patent is extended or adjusted under 35 U.S.C. 154(b) by 123 days.

(21) Appl. No.: 14/878,455

(22) Filed: Oct. 8, 2015

(65) Prior Publication Data

US 2016/0193445 A1 Jul. 7, 2016

Related U.S. Application Data

(63) Continuation of application No. 13/836,017, filed on Mar. 15, 2013, which is a continuation-in-part of application No. PCT/US2011/051542, filed on Sep. 14, 2011.

(60) Provisional application No. 61/384,174, filed on Sep. 17, 2010.

(51) Int. Cl.
*A61M 25/01* (2006.01)
*A61M 25/09* (2006.01)
*A61B 90/00* (2016.01)
*A61B 34/30* (2016.01)

(52) U.S. Cl.
CPC ......... *A61M 25/0113* (2013.01); *A61B 34/30* (2016.02); *A61M 25/0116* (2013.01); *A61M 25/0147* (2013.01); *A61M 25/09041* (2013.01); *A61B 2034/301* (2016.02); *A61B 2090/3764* (2016.02)

(58) Field of Classification Search
CPC .......... A61M 25/0113; A61M 25/0147; A61B 19/2203; A61B 2019/2211; A61B 19/56; A61B 2017/0046; A61B 2019/2223; A61B 2019/2276; A61B 2019/301; A61B 2019/5238; A61B 2019/5242
See application file for complete search history.

(56) References Cited

U.S. PATENT DOCUMENTS

| | | | |
|---|---|---|---|
| 3,317,779 | A | 5/1967 | Henderson |
| 3,835,854 | A | 9/1974 | Jewett |
| 4,270,725 | A | 6/1981 | Scott et al. |
| 4,355,747 | A | 10/1982 | Vinas |
| 4,616,648 | A | 10/1986 | Simpson |
| 5,318,541 | A | 6/1994 | Viera et al. |

(Continued)

FOREIGN PATENT DOCUMENTS

WO 2011058493 A1 5/2011

OTHER PUBLICATIONS

International Preliminary Report on Patentability for PCT/US2011/051542; date of mailing Mar. 28, 2013; 9 pages.

(Continued)

*Primary Examiner* — Julian W Woo
(74) *Attorney, Agent, or Firm* — Rathe Lindenbaum LLP

(57) ABSTRACT

A drive mechanism for a robotic catheter system including a first engagement surface and a second engagement surface is provided. The first engagement surface and second engagement surface are configured to engage a catheter device to allow the drive mechanism to impart motion to the catheter device. The first engagement surface is textured to facilitate gripping between the first engagement surface and the catheter device.

20 Claims, 20 Drawing Sheets

(56) References Cited

U.S. PATENT DOCUMENTS

| | | |
|---|---|---|
| 5,346,498 A | 9/1994 | Greelis et al. |
| 6,171,234 B1 | 1/2001 | White et al. |
| 6,290,675 B1 | 9/2001 | Vujanic et al. |
| 8,425,465 B2 | 4/2013 | Nagano et al. |
| 8,491,567 B2 | 7/2013 | Magnin et al. |
| 2003/0036712 A1 | 2/2003 | Heh et al. |
| 2004/0186511 A1 | 9/2004 | Stephens et al. |
| 2006/0146010 A1 | 7/2006 | Schneider |
| 2010/0076310 A1 | 3/2010 | Wenderow et al. |

OTHER PUBLICATIONS

International Search Report and Written Opinion for PCT/US2011/051542; date of mailing Jan. 5, 2012; 11 pages.

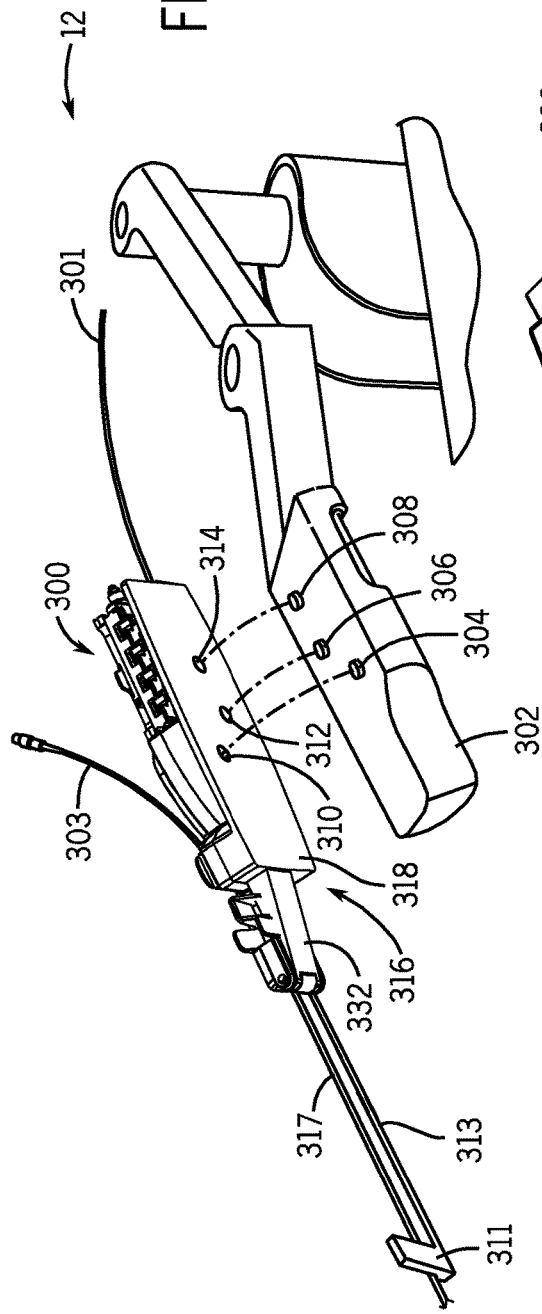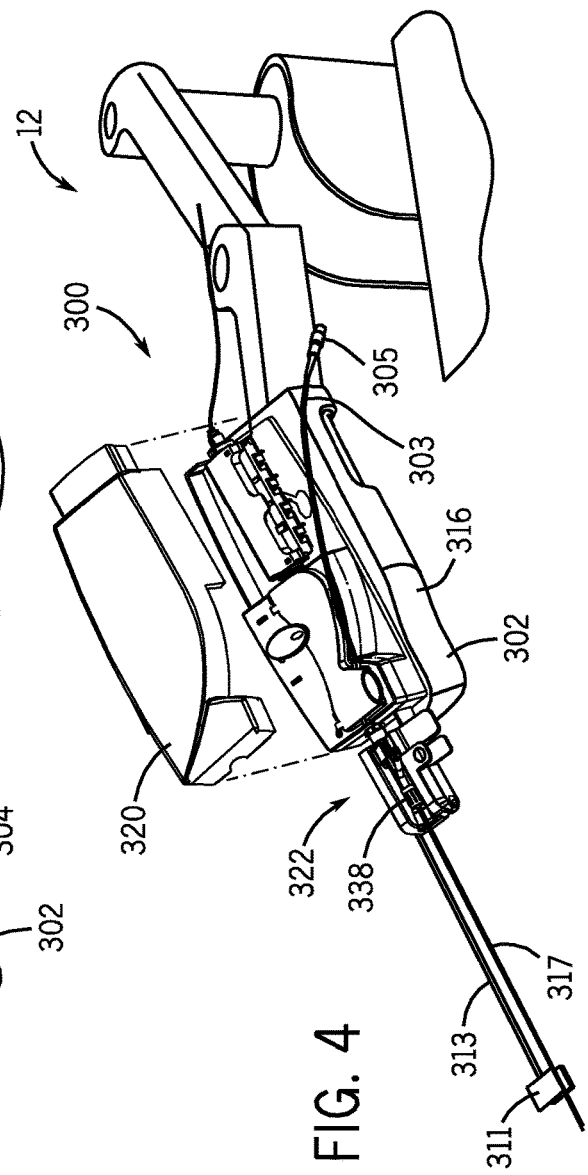

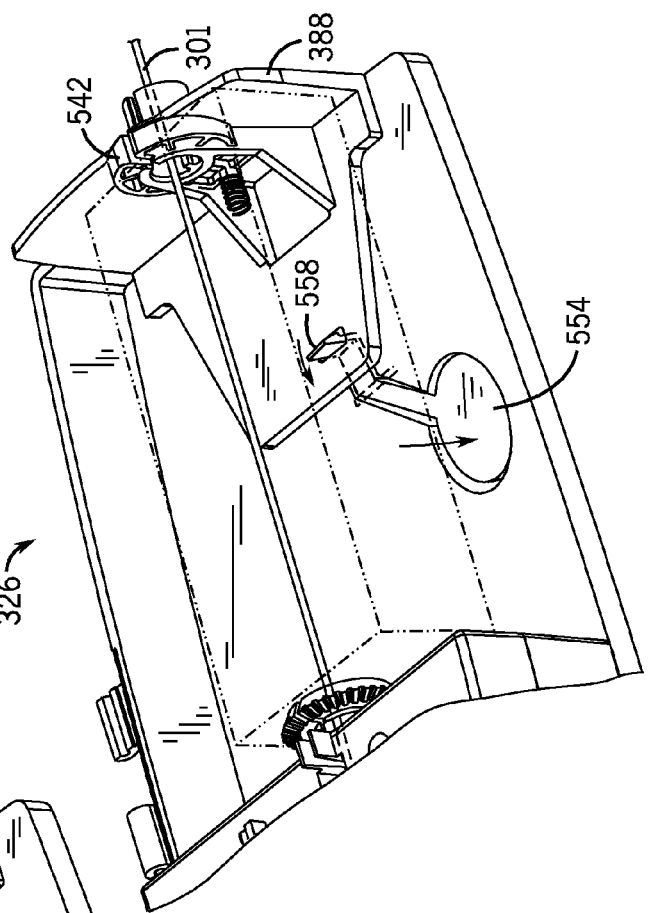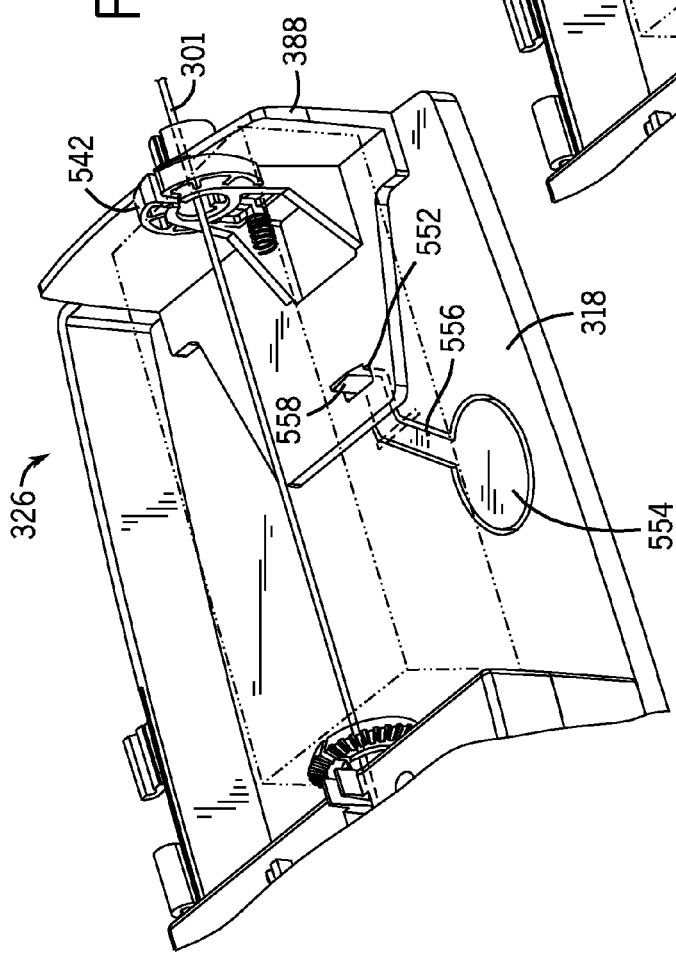

WHEEL FOR ROBOTIC CATHETER SYSTEM DRIVE MECHANISM

CROSS-REFERENCE TO RELATED APPLICATIONS

This application is a continuation of U.S. application Ser. No. 13/836,017, filed on Mar. 15, 2013, which is a continuation-in-part of International Application No. PCT/US11/51542, filed Sep. 14, 2011, which claims the benefit of U.S. Provisional Application No. 61/384,174, filed Sep. 17, 2010, both of which are incorporated herein by reference in their entireties.

BACKGROUND

The present invention relates generally to the field of catheter systems for performing diagnostic and/or intervention procedures. The present invention relates specifically to catheter systems and methods including a roller wheel based drive mechanism.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases (e.g., hypertension, etc.) may be treated using catheterization procedures.

SUMMARY

One embodiment of the invention relates to a drive mechanism for a robotic catheter system which imparts both axial and rotational motion. The mechanism includes a tire of a drive wheel and a tire of an idler wheel which interact with each other, each of which has an engagement surface which interacts with a catheter device to cause it to move along its axis and which is free of any gripping features which run perpendicular to the axis of the catheter device. It also includes a set of rotational drive assembly wheel tires each of which has an engagement surface which interacts with a catheter device to cause it to rotate about its axis and which has a gripping feature which runs perpendicular to the axis of the catheter device.

Another embodiment of the invention relates to a drive mechanism for a robotic catheter system which imparts both axial and rotational motion using a composite tire on one or more of the wheels of the drive mechanism. The mechanism includes a drive wheel tire and an idler wheel tire which interact with each other, each of which has an engagement surface which interacts with a catheter device to cause it to move along its axis and a set of rotational drive assembly wheel tires each of which has an engagement surface which interacts with a catheter device to cause it to rotate about its axis. One or more of the tires has a composite structure in which a material or structure of higher resilience is interposed between its engagement surface and the hub on which it is mounted.

BRIEF DESCRIPTION OF THE DRAWINGS

This application will become more fully understood from the following detailed description, taken in conjunction with the accompanying figures, wherein like reference numerals refer to like elements in which:

FIG. 3 is a perspective view of a bedside system showing an embodiment of a cassette prior to being attached to a motor drive base;

FIG. 4 is a perspective view of a bedside system showing the cassette of FIG. 3 following attachment to the motor drive base;

FIG. 17A shows a rotational drive assembly coupled to a base plate of a cassette;

FIG. 17B shows depression of a release button to disconnect the rotational drive assembly from the base plate of the cassette;

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
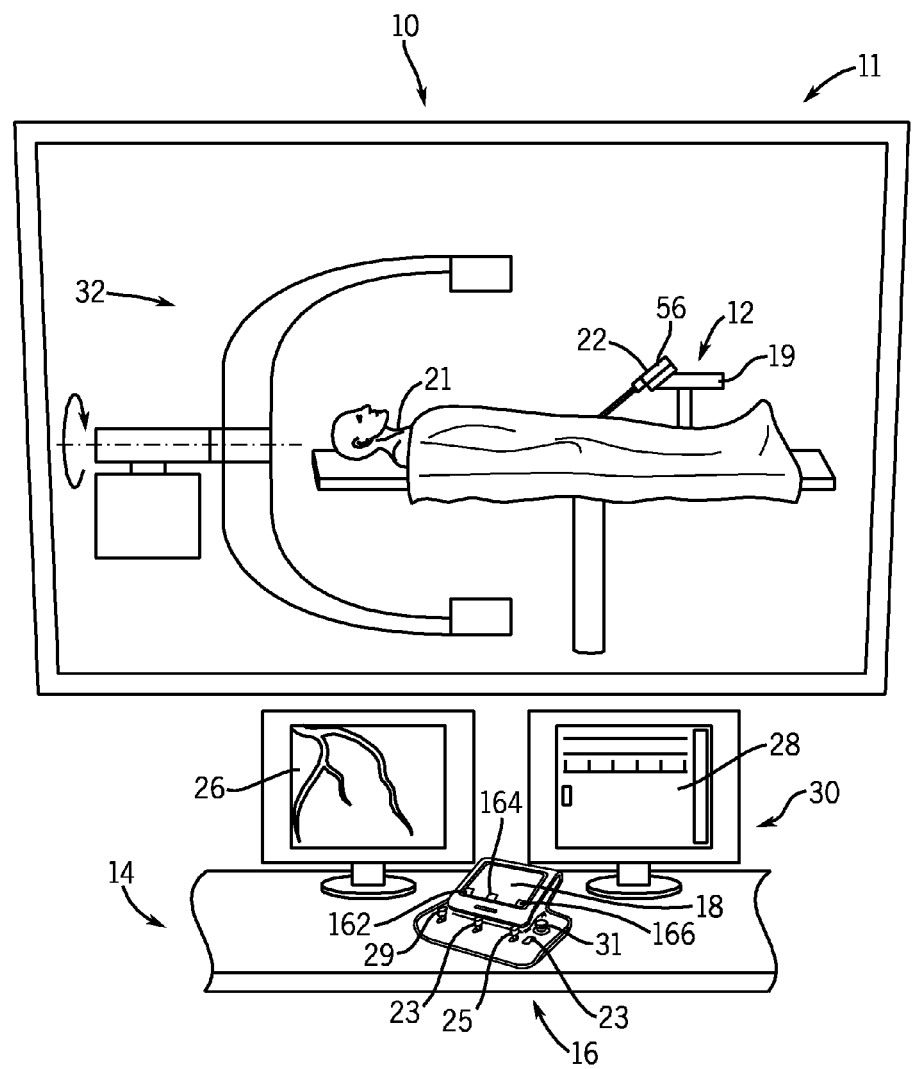
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, such as bedside system 12, located within lab unit 11 adjacent patient 21. Generally, bedside system 12 may be equipped with the appropriate percutaneous devices (e.g., guide wires, guide catheters, working catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter based medical procedure via a robotic system by operating various controls such as the controls located at workstation 14. Bedside system 12 may include any number and/or combination of components to provide bedside system 12 with the functionality described herein. Bedside system 12 may include a cassette 56 coupled to a base 19, and cassette 56 may include a housing 22 that supports the various components of the cassette. One particular embodiment of a cassette (shown as cassette 300) is described below in relation to FIGS. 3-23.

In one embodiment, bedside system 12 may be equipped to perform a catheter based diagnostic procedure. In this embodiment, bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, bedside system 12 may be equipped to perform a catheter based therapeutic procedure. In this embodiment, bedside system 12 may be equipped with a guide catheter, a guide wire, and a working catheter (e.g., a balloon catheter, a stent delivery catheter, ablation catheter, etc.). In one embodiment, the working catheter may be an over-the-wire working catheter that includes a central lumen that is threaded over the guide wire during a procedure. In another embodiment, the working catheter includes a secondary lumen that is separate from the central lumen of the working catheter, and the secondary lumen is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and control system of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30 configured to receive user inputs to operate various components or systems of catheter procedure system 10. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.). In some embodiments, one or more of the percutaneous intervention devices may be steerable, and controls 16 may be configured to allow a user to steer one or more steerable percutaneous device. In one such embodiment, bedside system 12 may be equipped with a steerable guide catheter, and controls 16 may also be configured to allow the user located at remote workstation 14 to control the bending of the distal tip of a steerable guide catheter.

In one embodiment, controls 16 include a touch screen 18, a dedicated guide catheter control 29, a dedicated guide wire control 23, and a dedicated working catheter control 25. In this embodiment, guide wire control 23 is a joystick configured to advance, retract, or rotate a guide wire, working catheter control 25 is a joystick configured to advance, retract, or rotate a working catheter, and guide catheter control 29 is a joystick configured to advance, retract, or rotate a guide catheter. In addition, touch screen 18 may display one or more icons (such as icons 162, 164, and 166) that control movement of one or more percutaneous devices via bedside system 12. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause the operation of guide wire control 23 to advance the guide wire at a rate of 2 mm/sec. Multiplier button 33 may be a toggle allowing the multiplier effect to be toggled on and off In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient-specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In one embodiment, monitors 26 and/or 28 may be configured to display an image of a portion of the patient (e.g., the patient's heart) at one or more magnification levels. In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device that is in communication with workstation 14. Referring to FIG. 1, imaging system 32 may include a C-arm that allows imaging system 32 to partially or completely rotate around patient 21 in order to obtain images at different angular positions relative to patient 21 (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 to properly move and position the percutaneous devices within the 3D geometry of the patient's heart. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
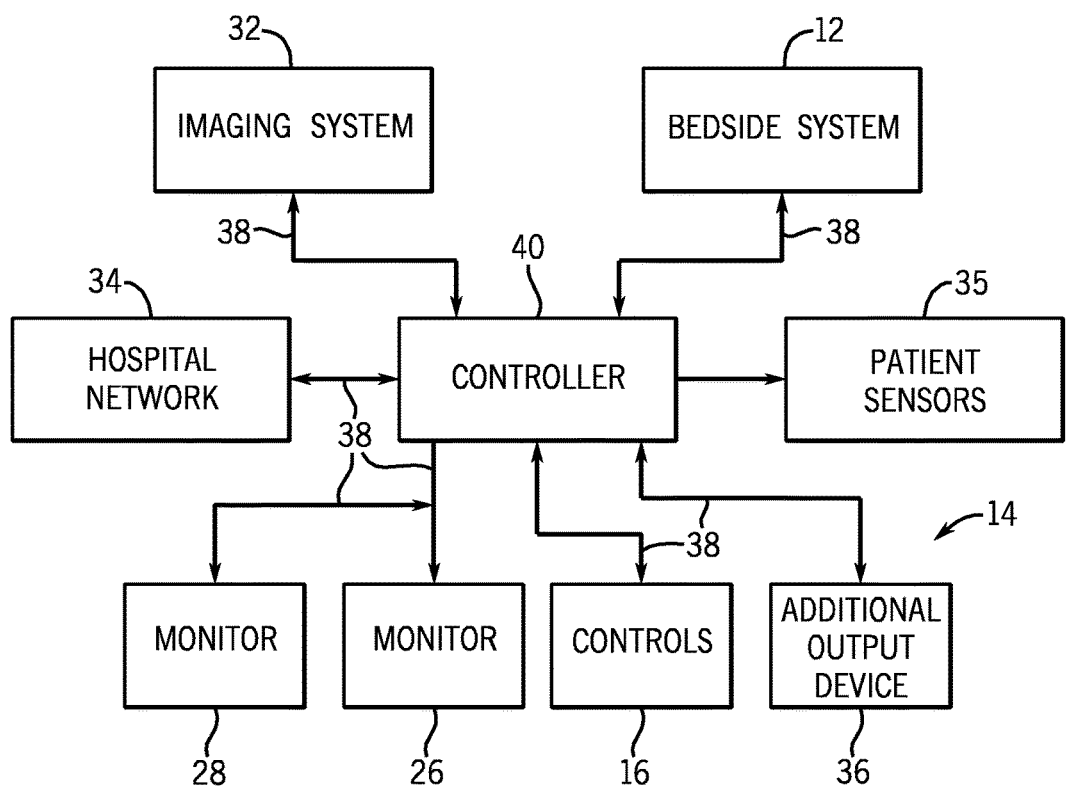
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, such as controller 40. Controller 40 may be part of workstation 14. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In various embodiments, controller 40 is configured to generate control signals based on the user's interaction with controls 16 and/or based upon information accessible to controller 40 such that a medical procedure may be preformed using catheter procedure system 10. In addition, controller 40 may be in communication with a hospital data management system or hospital network 34, and one or more additional output devices 36 (e.g., printer, disk drive, cd/dvd writer, etc.).

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, medicine tracking and/or logging systems, user logs, encryption systems, systems to restrict access or use of catheter procedure system 10, robotic catheter systems of the past, present, or future, etc.

Referring now to FIGS. 3 through 17C, an exemplary embodiment of a cassette for use with a robotic catheter system is shown. Cassette 300 may be equipped with a guide wire 301 and a working catheter 303 to allow a user to perform a catheterization procedure utilizing cassette 300. In this embodiment, bedside system 12 includes a cassette 300 configured to be mounted to a motor drive base 302. FIG. 3 shows a bottom perspective view of cassette 300 prior to mounting to motor drive base 302. Motor drive base 302 includes a first capstan 304, a second capstan 306, and a third capstan 308, and cassette 300 includes a first capstan socket 310, a second capstan socket 312, and a third capstan socket 314. Cassette 300 includes a housing 316, and housing 316 includes a base plate 318.

Each of the capstan sockets is configured to receive one of the capstans of motor drive base 302. In the embodiment shown, base plate 318 includes a hole or aperture aligned with each of the capstan sockets 310, 312, and 314 to allow each capstan to engage with the appropriate capstan socket. The engagement between the capstans and capstan sockets allows the transfer of energy (e.g., rotational movement) generated by one or more actuators (e.g., motors) located within motor drive base 302 to each of the drive mechanisms (discussed below) within cassette 300. In one embodiment, a single actuator provides energy to each of the drive mechanisms. In another embodiment, there is an actuator that drives capstan 304, an actuator that drives capstan 306, and an actuator that drives capstan 308. Further, the positioning of the capstans and capstan sockets helps the user to align cassette 300 relative to motor drive base 302 by allowing cassette 300 to be mounted to motor drive base 302 only when all three capstan sockets are aligned with the proper capstan.

In one embodiment, the motors that drive capstans 304, 306, and 308 are located within motor drive base 302. In another embodiment, the motors that drive capstans 304, 306, and 308 may be located outside of base 302 connected to cassette 300 via an appropriate transmission device (e.g., shaft, cable, etc.). In yet another embodiment, cassette 300 includes motors located within the housing of cassette 300. In another embodiment, cassette 300 does not include capstan sockets 310, 312, and 314, but includes an alternative mechanism for transferring energy (e.g., rotational motion) from an actuator external to the cassette to each of the cassette drive mechanisms. For example, rotational movement may be transferred to the drive mechanisms of cassette 300 via alternating or rotating magnets or magnetic fields located within motor drive base 302.

In the embodiment shown, cassette 300 also includes a guide catheter support 311 that supports guide catheter 317 at a position spaced from cassette 300. As shown, guide catheter support 311 is attached to cassette 300 by a rod 313. Rod 313 and guide catheter support 311 are strong enough to support guide catheter 317 without buckling. Guide catheter support 311 supports guide catheter 317 at a position spaced from the cassette, between the patient and the cassette to prevent buckling, bending, etc. of the portion of guide catheter 317 between the cassette and the patient.

Referring to FIG. 4, cassette 300 is shown mounted to motor drive base 302. As shown in FIG. 4, cassette 300 includes an outer cassette cover 320 that may be attached to housing 316. When attached to housing 316, outer cassette cover 320 is positioned over and covers each of the drive mechanisms of cassette 300. By covering the drive assemblies of cassette 300, outer cassette cover 320 acts to prevent accidental contact with the drive mechanisms of cassette 300 while in use.

Figure 5:
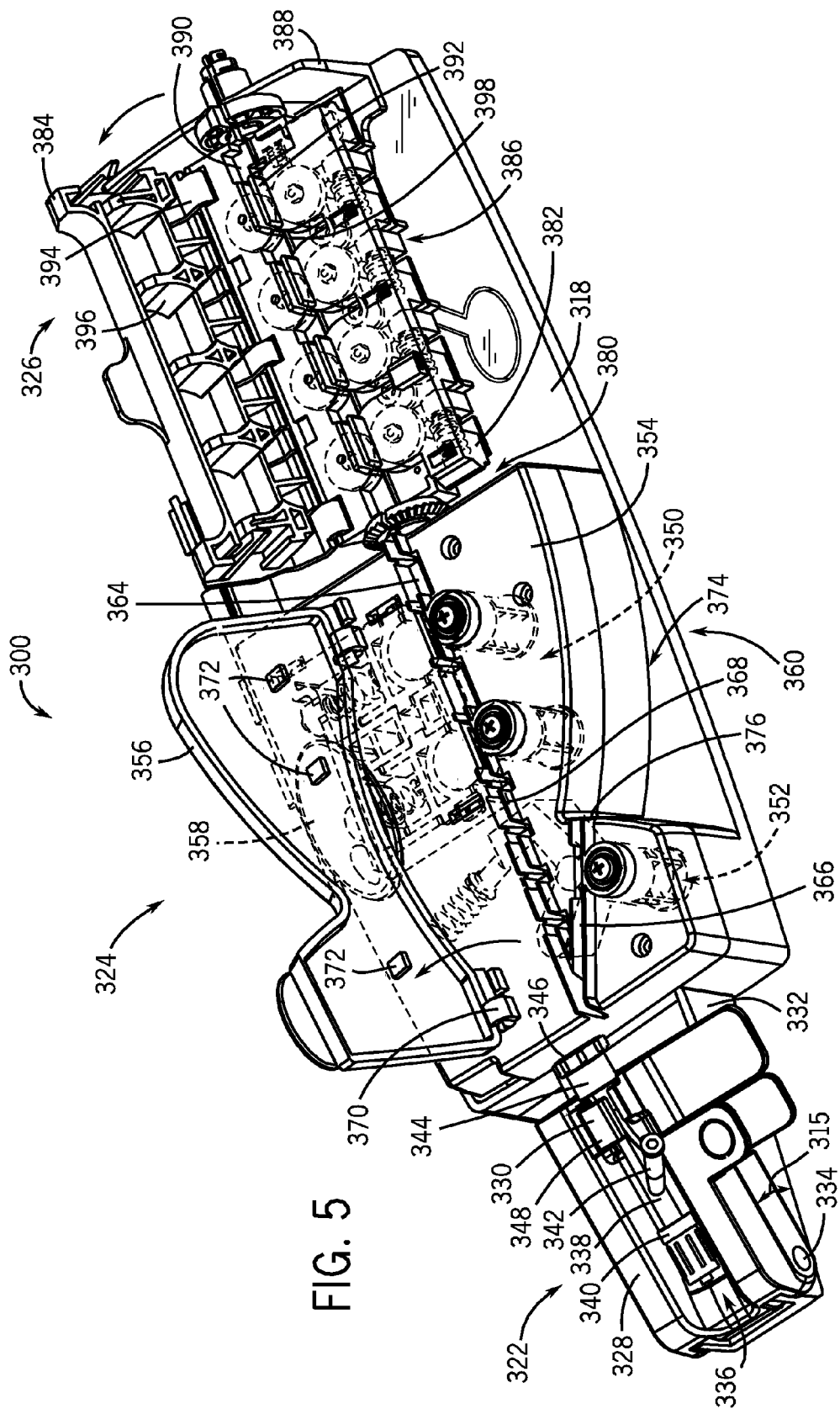
FIG. 5 is a perspective view of a cassette in the "loading" configuration.

Referring to FIG. 5, cassette 300 is shown in the "loading" configuration with outer cassette cover 320 removed. Cassette 300 includes a y-connector support assembly 322, an axial drive assembly 324, and a rotational drive assembly 326. Generally, the various portions of cassette 300 are placed in the loading configuration to allow the user to load or install a guide wire and/or working catheter into cassette 300. Further, in the exemplary embodiment shown, y-connector support assembly 322 is located in front of axial drive assembly 324, and axial drive assembly 324 is located in front of rotational drive assembly 326 within cassette 300.

Y-connector support assembly 322 includes a chassis 328 and a y-connector restraint 330. Base plate 318 includes a support arm 332 that supports y-connector support assembly 322. Chassis 328 is coupled to the front of support arm 332 via pin connection 334.

A central groove or depression 336 extends the length of chassis 328. Y-connector 338 rests within central groove 336 of chassis 328. Y-connector 338 includes a first leg 340, a second leg 342, and a third leg 344. First leg 340 is configured to attach to a guide catheter such that the central lumen of the y-connector is in fluid communication with the central lumen of the guide catheter. Second leg 342 is angled away from the longitudinal axis of y-connector 338. Second leg 342 of y-connector 338 allows introduction of a contrast agent or medicine into the lumen of the guide catheter. A one way valve prohibits bodily fluid from exiting second leg 342. Third leg 344 extends away from the guide catheter toward axial drive assembly 324. In use, guide wire 301 and working catheter 303 are inserted into third leg 344 of y-connector 338 via opening 346 and may be advanced through y-connector 338 into the lumen of the guide catheter. The third leg also includes a one way valve that permits insertion and removal of the working catheter and guide wire but prohibits bodily fluids from exiting third leg 344.

Chassis 328 is rotatable about an axis defined by pin connection 334 to allow chassis 328 to be placed in the "loading position" shown in FIG. 5. In the loading position, chassis 328 is positioned at about a 45 degree angle, shown by angle line 315, relative to support arm 332. Chassis 328 is moved to the "loading position" to provide easier access to opening 346 of the third leg 344 allowing the user to feed guide wire 301 and working catheter 303 into y-connector 338.

Y-connector support assembly 322 includes y-connector restraint 330. Y-connector restraint 330 is configured to releasably engage y-connector 338. In the engaged position shown in FIG. 5, engagement arm 348 of y-connector restraint 330 engages or presses y-connector 338 into central groove 336 to securely hold y-connector 338. Y-connector restraint 330 may be moved to a disengaged position to release y-connector 338 from chassis 328.

Cassette 300 also includes an axial drive assembly 324. Axial drive assembly 324 includes a first axial drive mechanism, shown as guide wire axial drive mechanism 350, and a second axial drive mechanism, shown as working catheter axial drive mechanism 352. Axial drive assembly 324 also includes a top deck 354, a cover 356, and a latch or handle 358.

Generally, guide wire axial drive mechanism 350 is configured to releasably engage and drive (e.g., to impart motion to) guide wire 301 along its longitudinal axis. In this manner, guide wire axial drive mechanism 350 provides for advancement and/or retraction of guide wire 301. Working catheter axial drive mechanism 352 is configured to releasably engage and drive (e.g., to impart motion to) working catheter 303 along its longitudinal axis. In this manner, working catheter axial drive mechanism 352 provides for advancement and/or retraction of working catheter 303.

Top deck 354 is mounted to a central portion 360 of base plate 318. Top deck 354 includes a guide wire channel 364 and a working catheter channel 366. Guide wire channel 364 is positioned generally perpendicular to the top surface of top deck 354 and runs the length of top deck 354 in the longitudinal direction. Working catheter channel 366 is positioned generally perpendicular to the top surface of top deck 354 and is located at an angle relative to guide wire channel 364. A plurality of tabs 368 extend vertically from the top surface of top deck 354 along guide wire channel 364.

In FIG. 5, cover 356 is shown in the open position. Handle 358 is moved to a position generally parallel to the longitudinal axis of cassette 300 to allow cover 356 to move to the open position. Cover 356 is mounted to top deck 354 via hinges 370. Cassette 300 includes a restraint structure that acts to restrain movement of the guide wire when cover 356 is in the closed position. As shown, the restraint structure includes a plurality of tabs 372 extending from the lower surface of cover 356. Tabs 372 are positioned such that when cover 356 is closed, tabs 372 are positioned within a portion of guide wire channel 364 between tabs 368 such that tabs 372 restrain movement of guide wire 301 in a vertical direction (i.e., restrains movement of the guide wire in a direction perpendicular to the top surface of top deck 354).

When cover 356 is in the open position, both guide wire axial drive mechanism 350 and working catheter axial drive mechanism 352 are exposed allowing the user to load cassette 300 with a guide wire and working catheter. With cover 356 open, guide wire 301 is loaded into axial drive assembly 324 by placing the guide wire into guide wire channel 364. Tabs 368 facilitate the placement of guide wire 301 by aiding the user in aligning the guide wire with guide wire channel 364. In addition, working catheter 303 is loaded into axial drive assembly 324 by placing the working catheter into working catheter channel 366. As will be described in more detail below, once the guide wire and working catheter are positioned within guide wire channel 364 and working catheter channel 366, respectively, engagement surfaces of guide wire axial drive mechanism 350 and working catheter axial drive mechanism 352 are brought into engagement with the guide wire and working catheter respectively.

Both top deck 354 and central portion 360 of base plate 318 are shaped to define a recess 374. Working catheter channel 366 includes an opening 376 located within recess 374. Recess 374 allows opening 376 to be closer to y-connector 338 and also closer to the entry incision in the patient allowing working catheter 303 to be advanced farther into the patient's vascular system than if opening 376 were located further away from y-connector 338 or the entry incision. As can be seen in FIG. 4, working catheter 303 includes a hub 305 at its proximal end that is too large to fit through opening 376. Thus, the closer that opening 376 is to y-connector 338 and to the entry incision the further working catheter 303 can be advanced into the patient's vascular system.

Cassette 300 also includes a rotational drive assembly 326. Rotational drive assembly 326 includes a rotational drive mechanism, shown as guide wire rotational drive mechanism 380, a cover 384, and a journal 388. Guide wire rotational drive mechanism 380 includes a chassis 382 and an engagement structure 386. Rotational drive assembly 326 is configured to cause guide wire 301 to rotate about its longitudinal axis. Engagement structure 386 is configured to releasably engage guide wire 301 and to apply sufficient force to guide wire 301 such that guide wire 301 is allowed to rotate about its longitudinal axis while permitting guide wire 301 to be moved axially by guide wire axial drive mechanism 350.

In the embodiment shown, rotational drive assembly 326 is supported within housing 316 such that rotation drive assembly 326 is permitted to rotate within housing 316. Engagement structure 386 applies sufficient force to guide wire 301 that the rotation of rotation drive assembly 326 causes guide wire 301 to rotate about its longitudinal axis as rotational drive assembly 326 rotates.

Chassis 382 includes a guide wire channel 390. Guide wire channel 390 is positioned generally perpendicular to the top surface of chassis 382 and runs the length of chassis 382 in the longitudinal direction. A plurality of tabs 392 extend vertically from the top surface of chassis 382 along guide wire channel 390. In FIG. 5, cover 384 is shown in the open position. Cover 384 is mounted to chassis 382 via hinge 394. Cassette 300 includes a restraint structure that acts to restrain movement of the guide wire when cover 384 is in the closed position. As shown, the restraint structure includes a plurality of tabs 396 extending from the lower surface of cover 384. The top surface of chassis 382 includes a plurality of recesses 398 configured to receive tabs 396 when cover 384 is in the closed position. Tabs 396 are positioned such that when cover 384 is closed, tabs 396 are positioned over guide wire channel 390 such that tabs 396 prevent guide wire 301 from falling out of guide wire channel 390 (i.e., restrains movement of the guide wire in a direction perpendicular to the top surface of chassis 382). In addition, the sidewalls of guide wire channel 390 and the engagement surfaces of wheels 522 and 524 prevent or restrain movement of guide wire 301 in other directions perpendicular to the longitudinal axis of guide wire 301. Thus, tabs 392 and guide wire channel 390 hold guide wire 301 within channel 390 during rotation of rotational drive assembly 326.

When cover 384 is in the open position, guide wire channel 390 is exposed allowing the user to load cassette 300 with a guide wire. With cover 384 open, guide wire 301 is loaded into rotational drive assembly 326 by placing the guide wire into guide wire channel 390. Tabs 392 facilitate the placement of guide wire 301 by aiding the user in aligning the guide wire with guide wire channel 390. As will be described in more detail below, once guide wire 301 is positioned within guide wire channel 390 engagement surfaces of engagement structure 386 are brought into engagement with the guide wire. In one embodiment, when the user activates controls (e.g., controls 16 located at workstation 14) to open cover 384, rotational drive assembly 326 is automatically rotated such that guide wire channel 390 is facing generally upward to allow for easy loading or removal of guide wire 301.

In one embodiment, cassette 300 is a modular cassette that allows various components of cassette 300 to be removed and/or switched out with other components. In an exemplary embodiment, a user may wish to control the guide wire using bedside system 12 and to control the working catheter manually. In this embodiment, a user may mount only guide wire axial drive mechanism 350 and rotational drive assembly 326 within housing 316 of cassette 300. In another exemplary embodiment, a user may wish to control the working catheter using bedside system 12 and to control the guide wire manually. In this embodiment, a user may mount only working catheter drive mechanism 352 within housing 316 of cassette 300. In another embodiment, cassette 300 may include additional locations for mounting drive mechanisms for any type of additional catheter devices that may be used during a procedure. For example, a user may be able to couple drive mechanisms to cassette 300 to control the movement and/or control of an intravascular ultrasound catheter.

Figure 6:
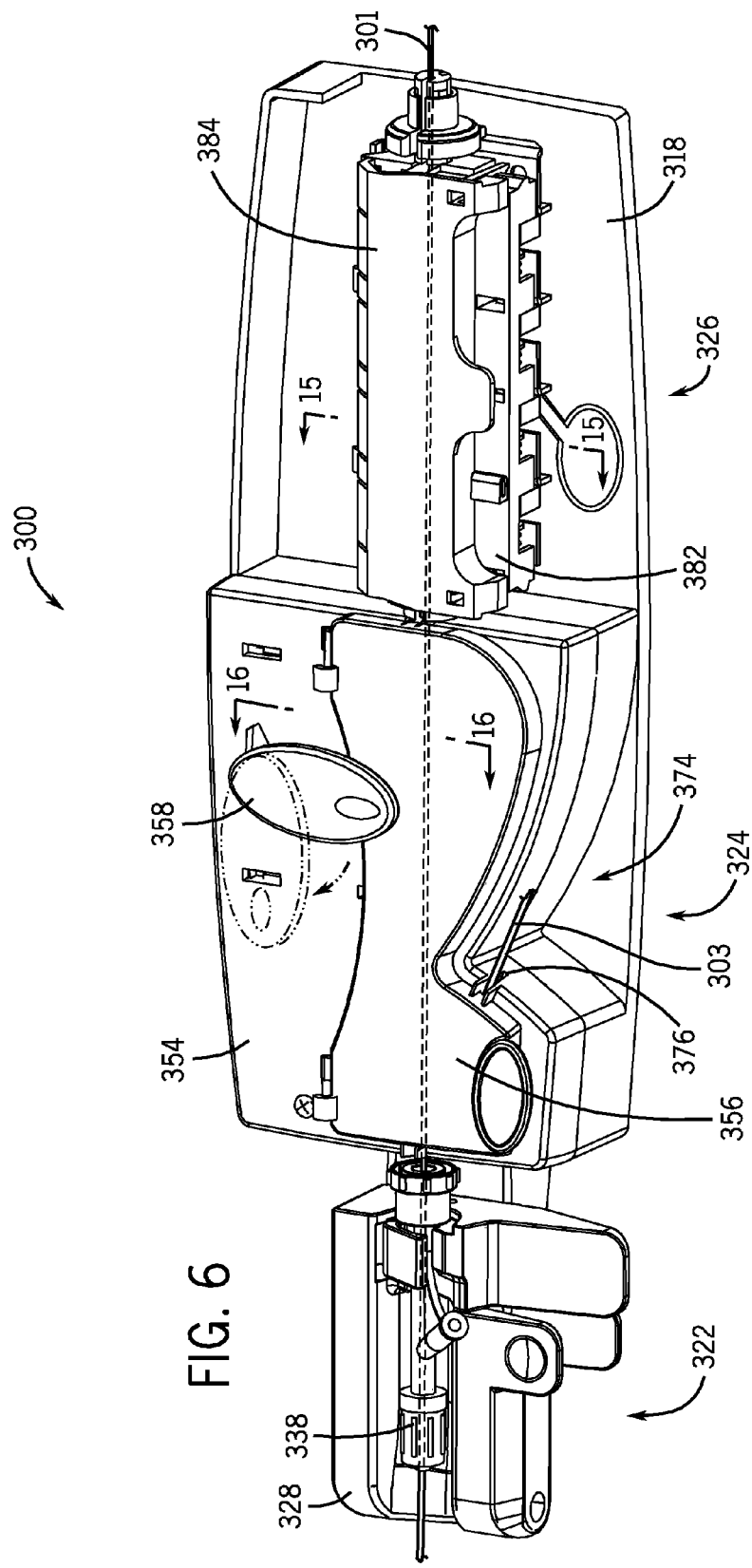
FIG. 6 is a perspective view of a cassette in the "loaded" or "use" configuration.

Referring to FIG. 6, cassette 300 is shown in the "loaded" or "use" position. In the "loaded" position, y-connector support assembly 322 is rotated downward such that y-connector 338 is aligned with guide wire channel 364 of axial drive assembly 324. The axial alignment allows guide wire 301 and working catheter 303 to be moved into and/or out of y-connector 338 via operation of guide wire axial drive mechanism 350 and working catheter axial drive mechanism 352. Cover 356 is shown in the closed position overlying both the guide wire axial drive mechanism 350 and the working catheter axial drive mechanism 352. As shown, cover 356 also covers guide wire channel 364 and working catheter channel 366. As such, cover 356 acts to prevent interference with the various components of axial drive assembly 324 during use.

After cover 356 is moved to the closed position, handle 358 is rotated approximately 90 degrees such that a portion of handle 358 is positioned over cover 356. As will be discussed in greater detail below, rotation of handle 358 to the closed position shown in FIG. 6 causes the engagement surface of the guide wire axial drive mechanism 350 and of the working catheter axial drive mechanism 352 to move together engaging the guide wire and working catheter, respectively.

In addition, when cassette 300 is moved to the "loaded" position, cover 384 is moved to the closed position overlying rotational drive mechanism 380 and guide wire channel 390 as shown in FIG. 6. Like cover 356, cover 384 acts to prevent interference with the various components of rotational drive assembly 326 during use. In one embodiment, a user may activate controls (e.g., controls located at workstation 14) to cause the various components of cassette 300 to move between the "loading" and "loaded" positions. In addition, cassette 300 may also be configured to allow the user to move the various components of cassette 300 between the "loading" and "loaded" positions manually.

Referring to FIG. 6, in the "loaded" or "use" configuration, the longitudinal axis (and the internal lumen) of y-connector 338 is aligned with guide wire channel 364 of axial drive assembly and with guide wire channel 390 of rotational drive assembly 326. This alignment provides a path extending from the rear of cassette 300 through y-connector 338 into the guide catheter through which the guide wire is advanced or retracted during axial movement of the guide wire. In various embodiments, components of cassette 300, including top deck 354, chassis 382, cover 356, and cover 384, may be made from a transparent or translucent plastic.

Figure 7:
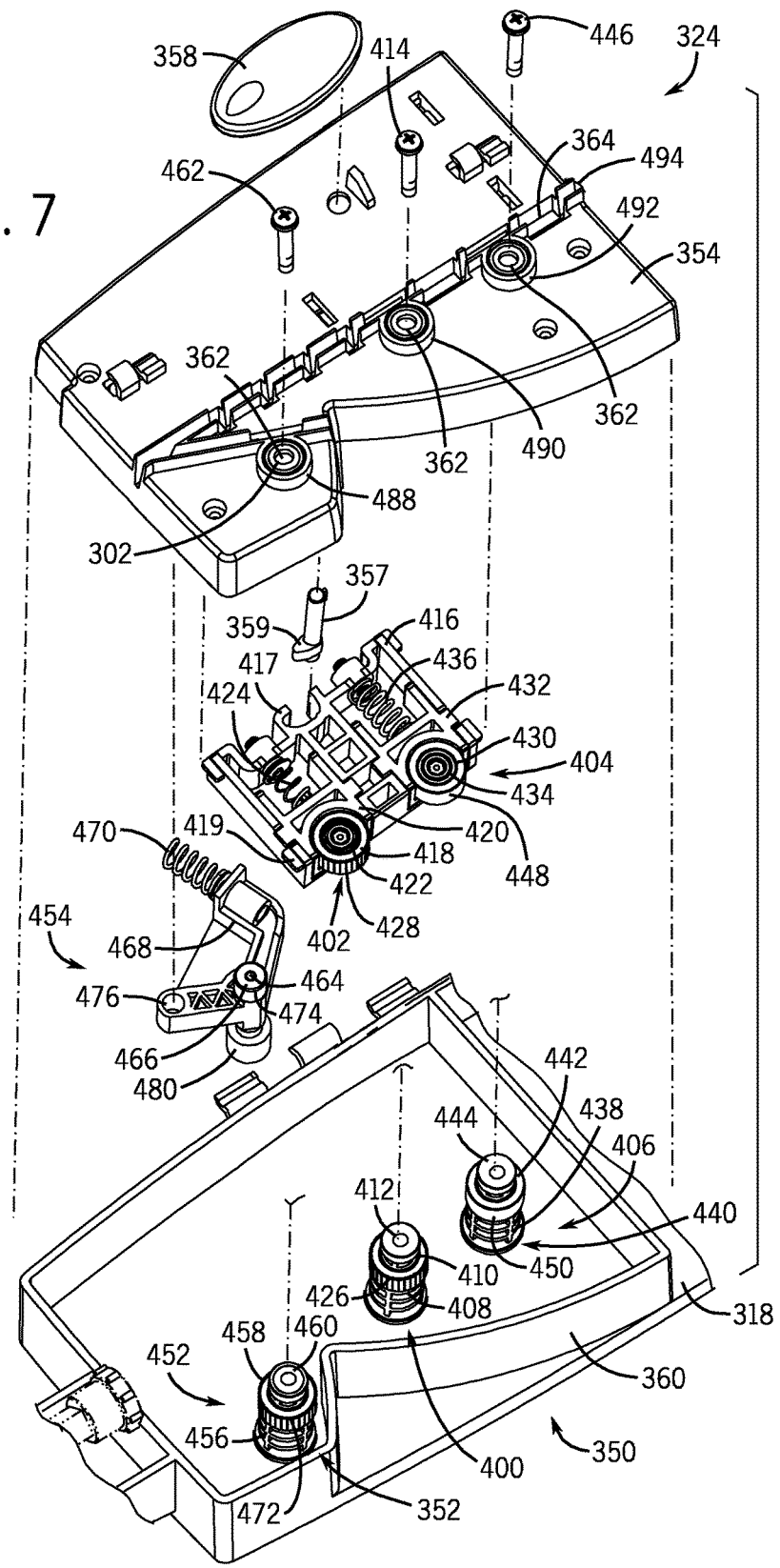
FIG. 7 is an exploded perspective view of an axial drive assembly of a cassette.

Referring to FIG. 7, an exploded perspective view from above of axial drive assembly 324 is shown. FIG. 7 generally depicts the components of axial drive assembly 324. Guide wire axial drive mechanism 350 and working catheter axial drive mechanism 352 are positioned above base plate 318, and top deck 354 is fastened to central portion 360 of base plate 318 above guide wire axial drive mechanism 350 and working catheter axial drive mechanism 352. Thus, guide wire axial drive mechanism 350 and working catheter axial drive mechanism 352 are generally enclosed within a chamber defined by top deck 354 and central portion 360 of base plate 318 when axial drive assembly 324 is assembled. Top deck 354 includes a plurality of apertures 362 to receive various portions of both axial drive mechanism 350 and working catheter axial drive mechanism 352.

Axial drive mechanism 350 includes a drive element 400, a first roller assembly 402, a second roller assembly 404, and a guide wire axial motion sensor assembly, shown as encoder assembly 406. First roller assembly 402 and second roller assembly 404 are both mounted within a housing 416. Drive element 400 includes a drive shaft 408, a drive wheel 410, a bearing 412, and a screw 414. Drive shaft 408 is configured to engage second capstan 306 of motor drive base 302 such that drive shaft 408 and drive wheel 410 rotate in response to rotation of second capstan 306. First roller assembly 402 includes an idler wheel or roller 418, a wheel housing 420, a bearing 422, and a spring 424.

Drive wheel 410 includes an outer or engagement surface 426, and roller 418 includes an outer or engagement surface 428. Generally, when guide wire axial drive mechanism 350 is placed in the "use" or "engaged" position (shown in FIG. 10), guide wire 301 is positioned between drive wheel 410 and roller 418 such that engagement surface 426 of drive wheel 410 and engagement surface 428 of roller 418 are able to engage the guide wire. In this embodiment, engagement surface 426 and engagement surface 428 define a pair of engagement surfaces. The force applied to guide wire 301 by engagement surface 426 and engagement surface 428 is such that drive wheel 410 is able to impart axial motion to guide wire 301 in response to the rotation of drive shaft 408 caused by rotation of second capstan 306. This axial motion allows a user to advance and/or retract a guide wire via manipulation of controls 16 located at workstation 14. Roller 418 is rotatably mounted within wheel housing 420 and rotates freely as drive wheel 410 rotates to drive guide wire 301. Spring 424 is biased to exert a force onto wheel housing 420 causing roller 418 to engage the guide wire against drive wheel 410. Spring 424 is selected, tuned, and/or adjusted such that the proper amount of force is applied to guide wire 301 by engagement surface 426 and engagement surface 428 in the "engaged" position. In other embodiments, additional drive elements may be added as necessary to impart axial motion to the guide wire.

Second roller assembly 404 includes an idler wheel or roller 430, a wheel housing 432, a bearing 434, and a spring 436. Encoder assembly 406 includes shaft 438, magnetic coupling 440, idler wheel or roller 442, bearing 444, and a screw 446. Roller 430 includes an outer or engagement surface 448 and roller 442 includes an outer or engagement surface 450.

In the "engaged" position, guide wire 301 is positioned between roller 430 and roller 442 such that engagement surface 448 of roller 430 and engagement surface 450 of roller 442 are able to engage the guide wire. In this embodiment, engagement surface 448 and engagement surface 450 define a pair of engagement surfaces. The force applied to guide wire 301 by engagement surface 448 and engagement surface 450 is such that drive wheel 410 is able to pull guide wire 301 past roller 430 and 442. In this way, the pair of non-active or idle rollers 430 and 442 help support guide wire 301 and maintain alignment of guide wire 301 along the longitudinal axis of cassette 300.

Roller 430 is rotatably mounted within wheel housing 432, and roller 442 is rotatably mounted to shaft 438. Both rollers 430 and 442 are mounted to rotate freely as drive wheel 410 imparts axial motion to guide wire 301. Spring 436 is biased to exert a force onto wheel housing 432 causing roller 430 to engage guide wire 301 against roller 442. Spring 436 is selected, tuned, and/or adjusted such that the proper amount of force is applied to guide wire 301 by engagement surface 448 and engagement surface 450 in the "engaged" position to support the guide wire while still allowing the guide wire to be moved axially by drive wheel 410. In other embodiments, additional pairs of non-active or idler rollers may be added as needed to provide proper support and alignment for the guide wire. In one embodiment, spring 424 and spring 436 are selected or adjusted such that the force applied to guide wire 301 by wheels 430 and 442 is approximately the same as the force applied to guide wire 301 by wheels 410 and 418.

Figure 18:
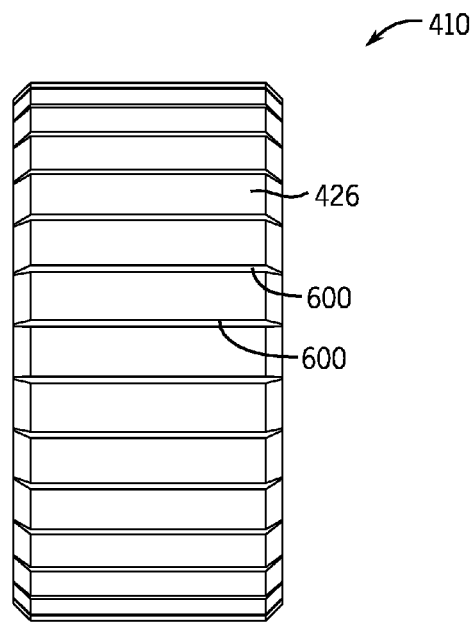
FIG. 18 shows a side view of a roller wheel according to an exemplary embodiment.
Figure 19A:
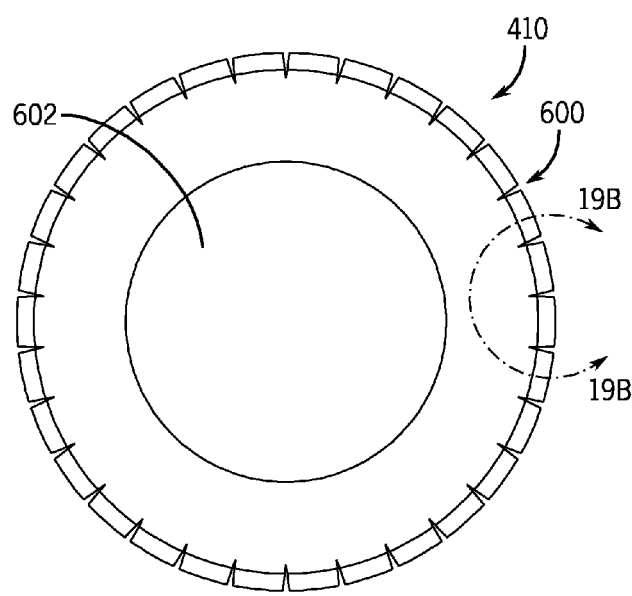
FIG. 19A shows a top view of the roller wheel of FIG. 18.
Figure 19B:
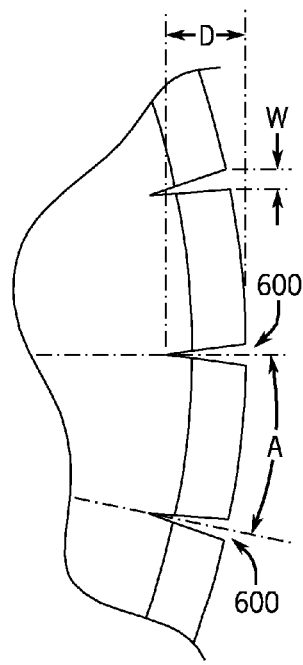
FIG. 19B shows an enlarged view of a portion of the roller wheel of FIG. 19B.

As shown in FIG. 7, engagement surface 426 of drive wheel 410 and engagement surface 428 of roller wheel 418 are configured to increase the ability of the wheel to grip and to impart axial motion to the guide wire. In particular, engagement surface 426 of drive wheel 410 and engagement surface 428 of roller wheel 418 may be textured (e.g., non-smooth, treaded, slotted, etc.) to increase friction between the wheels and the guide wire. A particular embodiment of a wheel for a robotic catheter system including a textured engagement surface is shown in FIGS. 18, 19A and 19B, discussed in more detail below. While FIG. 7, shows both wheels of the front pair in guide wire axial drive mechanism 350 as textured, any combination of wheels in guide wire axial drive mechanism may be textured. For example, in other embodiments, only drive wheel 410 may be textured, or all four wheels (wheels 410, 418, 430, and 442) may be textured.

In various embodiments, the force applied to guide wire 301 by wheels 410, 418, 430 and 442 generated by springs 424 and 436 (e.g., the pinch force) may be variable or controllable. In various embodiments, the pinch force may be varied to accommodate the use of a variety of different types of guide wires. For example, if cassette 300 is equipped with a guide wire having a rough or textured outer surface, the pinch force generated by springs 424 and 436 may be decreased to ensure the proper amount of friction between the wheels and the guide wire. In contrast, if cassette 300 is equipped with a guide wire having a smooth surface outer surface, the pinch force generated by springs 424 and 436 may be increased to ensure the proper amount of friction between the wheels and the guide wire. In other embodiments, the pinch force may be controlled to vary the performance of cassette 300 during a procedure. For example, the pinch force may be increased to help ensure that the guide wire remains in place (i.e., no axial motion occurs) when the controls for guide wire axial motion are not be actuated by the user and/or when the user is actuating controls for a different percutaneous device.

The pinch force may be varied or controlled by the user in various ways. For example, in one embodiment, cassette 300 may include one or more actuator (e.g., a step motor) that receives a control signal from controller 40 to adjust the force generated by springs 424 and 436. In this embodiment, controls 16 may include a control (e.g., a button, dial, touch screen icon, etc.) that allows the user to alter the pinch force of guide wire axial drive mechanism 350 from workstation 14. In another embodiment, controller 40 may be configured to automatically adjust the pinch force generated by springs 424 and 436 based upon the type of guide wire that cassette 300 is equipped with. Controller 40 may prompt the user to identify the type of guide wire via controls 16 (e.g., via a drop down menu, reading a bar code, etc.). In another embodiment, catheter procedure system 10 may be configured to automatically identify the type of guide wire that cassette 300 is equipped with (e.g., via reading of an RFID tag associated with the guide wire), and controller 40 may be configured to automatically control the pinch force based on the automatically determined guide wire type.

Encoder assembly 406 includes magnetic coupling 440 that engages a magnetic encoder located within motor drive base 302. The magnetic encoder is configured to measure an aspect (e.g., speed, position, acceleration, etc.) of axial movement of the guide wire. As roller 442 rotates, shaft 438 rotates causing magnetic coupling 440 to rotate. The rotation of magnetic coupling 440 causes rotation of the magnetic encoder within motor drive base 302. Because rotation of roller 442 is related to the axial movement of guide wire 301, the magnetic encoder within motor drive base 302 is able to provide a measurement of the amount of axial movement experienced by guide wire 301 during a procedure. This information may be used for a variety of purposes. For example, this information may be displayed to a user at workstation 14, may be used in a calculation of or estimated position of the guide wire within the vascular system of a patient, may trigger an alert or alarm indicating a problem with guide wire advancement, etc.

As shown in FIG. 7, first roller assembly 402 and second roller assembly 404 are both mounted within a housing 416. Housing 416 provides a common support for first roller assembly 402 and second roller assembly 404. As will be discussed in more detail below, first roller assembly 402 and second roller assembly 404 are moved away from drive wheel 410 and roller 442, respectively, when axial drive assembly 324 is placed in the "loading" configuration. This facilitates placement of guide wire 301 between the opposing pairs of engagement surfaces of guide wire axial drive mechanism 350. Housing 416 allows first roller assembly 402 and second roller assembly 404 to be moved together (e.g., in sync) away from drive wheel 410 and roller 442, respectively, when axial drive assembly 324 is placed in the "load" configuration.

Axial drive assembly 324 also includes working catheter axial drive mechanism 352. Working catheter axial drive mechanism 352 includes a drive element 452 and a working catheter axial motion sensor assembly, shown as working catheter encoder assembly 454. Drive element 452 includes a drive shaft 456, a drive wheel 458, a bearing 460, and a screw 462. Drive shaft 456 is configured to engage first capstan 304 of motor drive base 302 such that drive shaft 456 and drive wheel 458 rotate in response to rotation of first capstan 304. Encoder assembly 454 includes shaft 464, a roller 466, an encoder linkage 468, a spring 470, and a magnetic coupling 480.

Drive wheel 458 includes an outer or engagement surface 472 and roller 466 includes an outer or engagement surface 474. When working catheter axial drive mechanism 352 is in the "engaged" position, a working catheter is positioned between drive wheel 458 and roller 466, such that engagement surface 472 and engagement surface 474 are able to engage working catheter 303. In this embodiment, engagement surfaces 472 and 474 define a pair of engagement surfaces. The force applied to working catheter 303 by engagement surfaces 472 and 474 is such that drive wheel 458 is able to impart axial motion to the working catheter in response to the rotation of drive shaft 456 caused by rotation of first capstan 304. This axial motion allows a user to advance and/or retract a working catheter via manipulation of controls located at workstation 14. Roller 466 is rotatably mounted to shaft 464 and rotates freely as drive wheel 458 rotates to drive the working catheter.

As shown in FIG. 7, engagement surface 472 of drive wheel 458 is configured to increase the ability of the wheel to grip and to impart axial motion to the working catheter.

In particular, engagement surface 472 of drive wheel 458 may be textured (e.g., non-smooth, treaded, slotted, etc.) to increase friction between the wheel and the working catheter. A particular embodiment of a wheel including a textured engagement surface is shown in FIGS. 18, 19A and 19B, discussed in more detail below. While FIG. 7 shows drive wheel 458 with a textured outer surface and roller 466 with a non-textured engagement surface 474, in other embodiments, both drive wheel 458 and roller 466 may include textured outer surfaces.

Spring 470 is coupled to a first end of linkage 468. The second end of linkage 468 includes an aperture 476 that is pivotally coupled to a post 478 extending from the inner surface of top deck 354. Spring 470 is biased to exert a force on to linkage 468 causing linkage 468 to pivot about post 478 to force roller 466 to engage working catheter 303 against drive wheel 458. Spring 470 is selected, tuned, and/or adjusted such that the proper amount of force is applied to working catheter 303 by engagement surfaces 472 and 474 in the "engaged" position to allow drive wheel 458 to impart axial movement to the working catheter.

Encoder assembly 454 includes magnetic coupling 480 that engages a magnetic encoder located within motor drive base 302. The magnetic encoder is configured to measure an aspect (e.g., speed, position, acceleration, etc.) of axial movement of the working catheter. As roller 466 rotates, shaft 464 rotates causing magnetic coupling 480 to rotate. The rotation of magnetic coupling 480 causes rotation of the magnetic encoder within motor drive base 302. Because rotation of roller 466 is related to the axial movement of working catheter 303, the magnetic encoder within motor drive base 302 is able to provide a measurement of the amount of axial movement experienced by the working catheter during a procedure. This information may be used for a variety of purposes. For example, this information may be displayed to a user at workstation 14, may be used in a calculation of or estimated position of the working catheter within the vascular system of a patient, may trigger an alert or alarm indicating a problem with working catheter advancement, etc.

As will be discussed in more detail below, roller 466 is moved away from drive wheel 458 when axial drive assembly 324 is placed in the "loading" configuration. This facilitates placement of the working catheter between the opposing pairs of engagement surfaces of working catheter axial drive mechanism 352.

In one embodiment, cassette 300 and/or motor drive base 302 includes a locking mechanism that is configured to lock the position of guide wire 301 during manipulation of the working catheter 303 and to lock the position of working catheter 303 during manipulation of guide wire 301. In one embodiment, the locking mechanism acts to increase the force applied to the guide wire by the engagement surfaces when the working catheter is being advanced and to increase the force applied to the working catheter by the engagement surfaces when the guide wire is being advanced.

Figure 8:
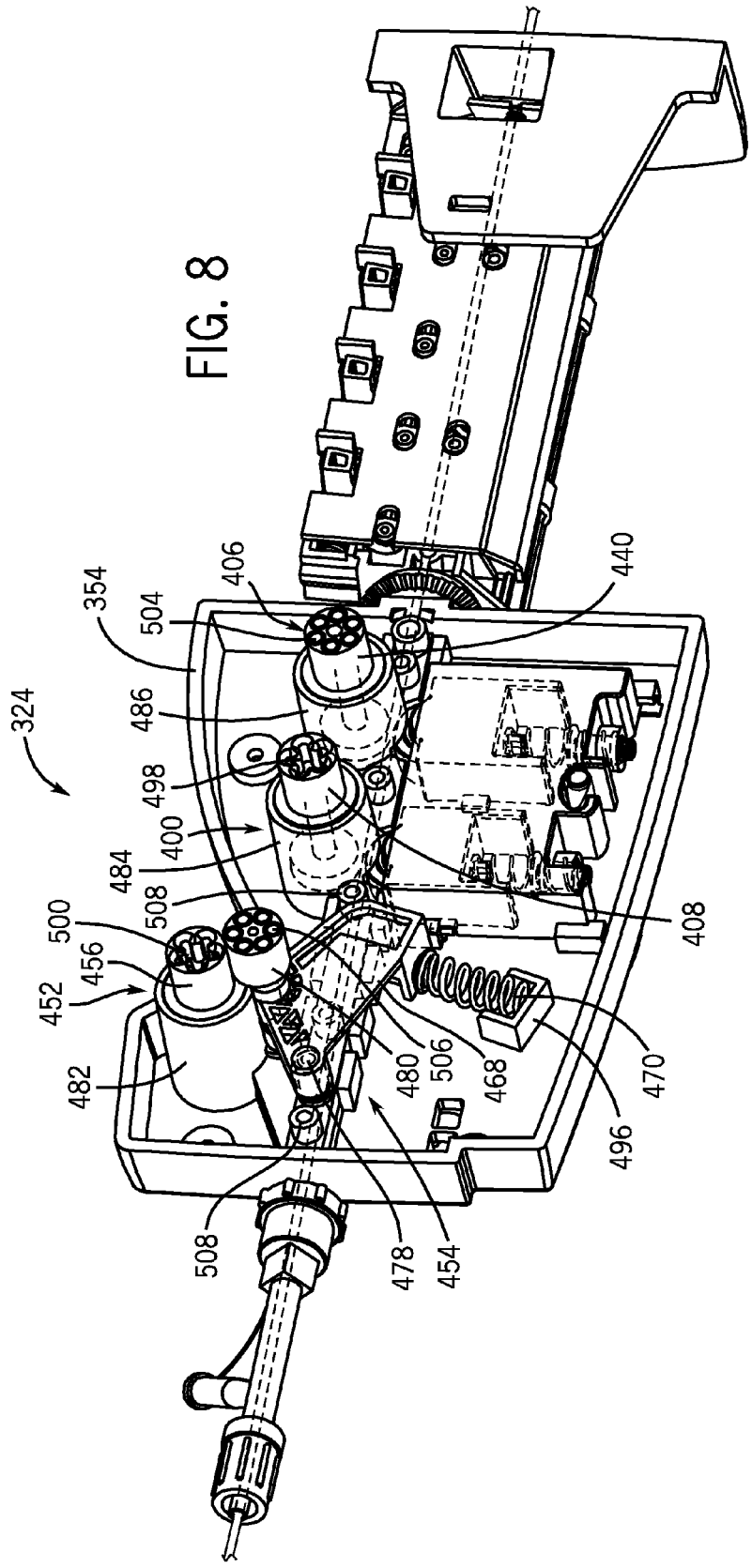
FIG. 8 is a bottom perspective view of a cassette showing the base plate removed.

Referring to FIGS. 7 and 8, top deck 354 includes a plurality of cylindrical sleeves, first sleeve 482, second sleeve 484, and third sleeve 486, extending from the inner or lower surface of top deck 354. Top deck 354 also includes a plurality of cylindrical collars, first collar 488, second collar 490, and third collar 492, extending from the upper surface of top deck 354. Collar 488 is in axial alignment with sleeve 482. Collar 490 is in axial alignment with sleeve 484. Collar 492 is in axial alignment with sleeve 486. Each of the collars 488, 490, and 492 define an aperture 362. In the embodiment shown, sleeve 482 and collar 488 are configured to receive working catheter drive element 452, sleeve 484 and collar 490 are configured to receive guide wire drive element 400, and sleeve 486 and collar 492 are configured to receive guide wire encoder assembly 406. Apertures 362 provide access to screws 414, 446, and 462 once top deck 354 is mounted over axial drive assembly 324.

Top deck 354 includes a collar 494 aligned with and located at the back end of guide wire channel 364. Collar 494 is configured to receive front shaft 512 that extends from chassis 382 of rotational drive assembly 326. Collar 494 is configured to allow front shaft 512 (and consequently the rest of rotational drive assembly 326) to rotate about the longitudinal axis of guide wire channel 390 relative to axial drive assembly 324. In one embodiment, rotational drive assembly 326 is able to rotate relative to housing 316 of cassette 300 while axial drive assembly 324 does not rotate relative to housing 316. In another embodiment, both rotational drive assembly 326 and axial drive assembly 324 rotate relative to housing 316 of cassette 300.

FIG. 8 is a bottom perspective view of cassette 300 showing top deck 354 mounted above guide wire axial drive mechanism 350 and working catheter axial drive mechanism 352. FIG. 8 shows working catheter drive element 452, guide wire drive element 400, and guide wire encoder assembly 406 received within sleeves 482, 484, and 486. A support structure 496 extends from the lower surface of top deck 354. Spring 470 is coupled at one end to support structure 496 allowing spring 470 to compress and expanded between linkage 468 and support structure 496.

As shown, the lower end of drive shaft 408 includes a keyed recess 498, and the lower end of drive shaft 456 includes a keyed recess 500. Keyed recess 500 is one embodiment of first capstan socket 310, and keyed recess 498 is one embodiment of second capstan socket 312. Keyed recess 500 is configured to receive a capstan, such as first capstan 304, and keyed recess 498 is configured to receive a capstan, such as second capstan 306. First capstan 304 and second capstan 306 are keyed to fit within keyed recess 500 and 498 and to engage and turn drive shafts 456 and 408 upon rotation of the capstans.

As shown, magnetic coupling 440 of guide wire encoder assembly 406 includes a circular array of magnets 504. Magnetic coupling 480 of working catheter encoder assembly 454 includes a circular array of magnets 506. Magnetic couplings 440 and 480 engage with magnetic encoders positioned within motor drive base 302. The magnetic encoders of motor drive base 302 are coupled to appropriate electronics to detect and measure rotation of rollers 442 and 466 and to calculate axial motion of guide wire 301 and working catheter 303 based on the measured rotations. While this embodiment discloses the use of magnetic encoders to detect the axial motion of the guide wire and working catheter, other sensors may be used. In one embodiment, axial motion of the guide wire may be detected by an optical sensor that detects movement of the guide wire and/or working catheter by scanning the surface of the guide wire and/or working catheter as it passes the optical sensor. In one such embodiment, the optical sensor includes an LED light source and a detector (e.g., a complementary metal oxide semiconductor, other light detecting circuitry, etc.) that detects light reflected off the surface of the guide wire and/or working catheter, and the light detected by the detector is analyzed (e.g., by a digital signal processor) to determine movement of the guide wire and/or working catheter. In another embodiment, the surface of the guide wire and/or working catheter may include indicia that are detected to determine axial movement of the guide wire. In other embodiments, other types of sensors (e.g., resolvers, sychros, potentiometers, etc.), may be used to detect movement of the guide wire and/or working catheter.

Cassette 300 also includes a series of magnets 508 positioned below guide wire channel 364. Because, in at least some embodiments, the guide wire is made from a magnetic material, magnets 508 are able to interact with the guide wire. In this embodiment, the magnetic attraction created by magnets 508 helps the user position guide wire 301 during loading by drawing guide wire 301 into guide wire channel 364. The magnetic attraction created by magnets 508 also tends to hold guide wire 301 within guide wire channel 364 during advancement and/or retraction of the guide wire. Further, magnets 508 help to hold guide wire 301 straight (i.e., parallel to the longitudinal axis of guide wire channel 364) to aid in the axial movement caused by guide wire axial drive mechanism 350.

Figure 9:
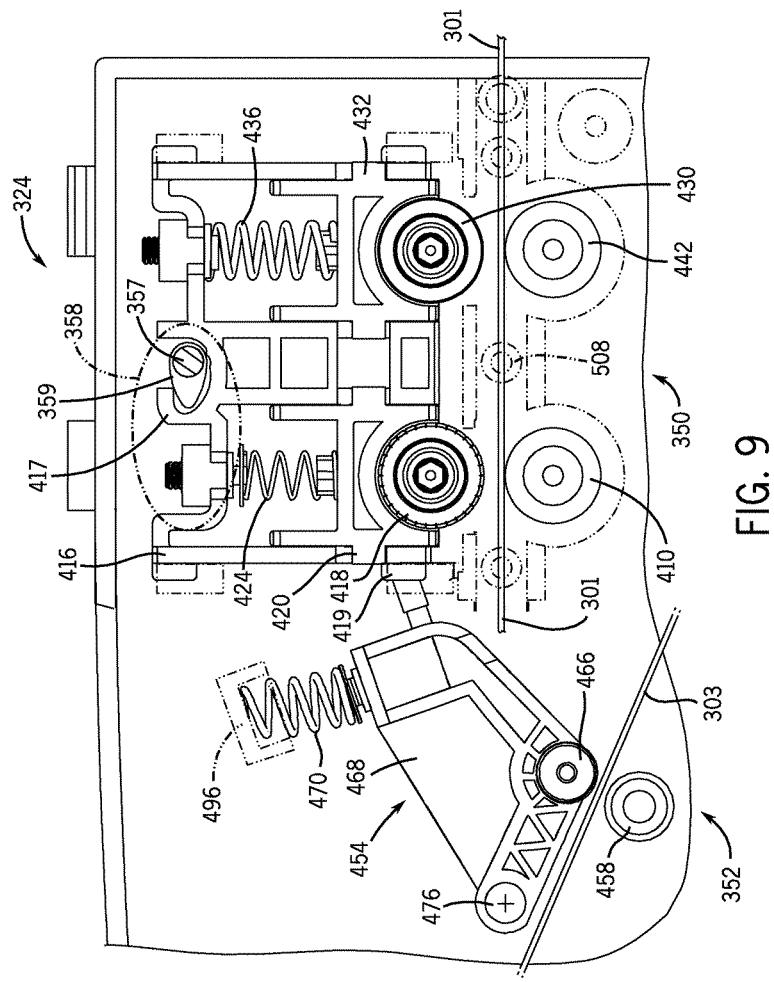
FIG. 9 is a top view showing the axial drive assembly in the "disengaged" position.
Figure 10:
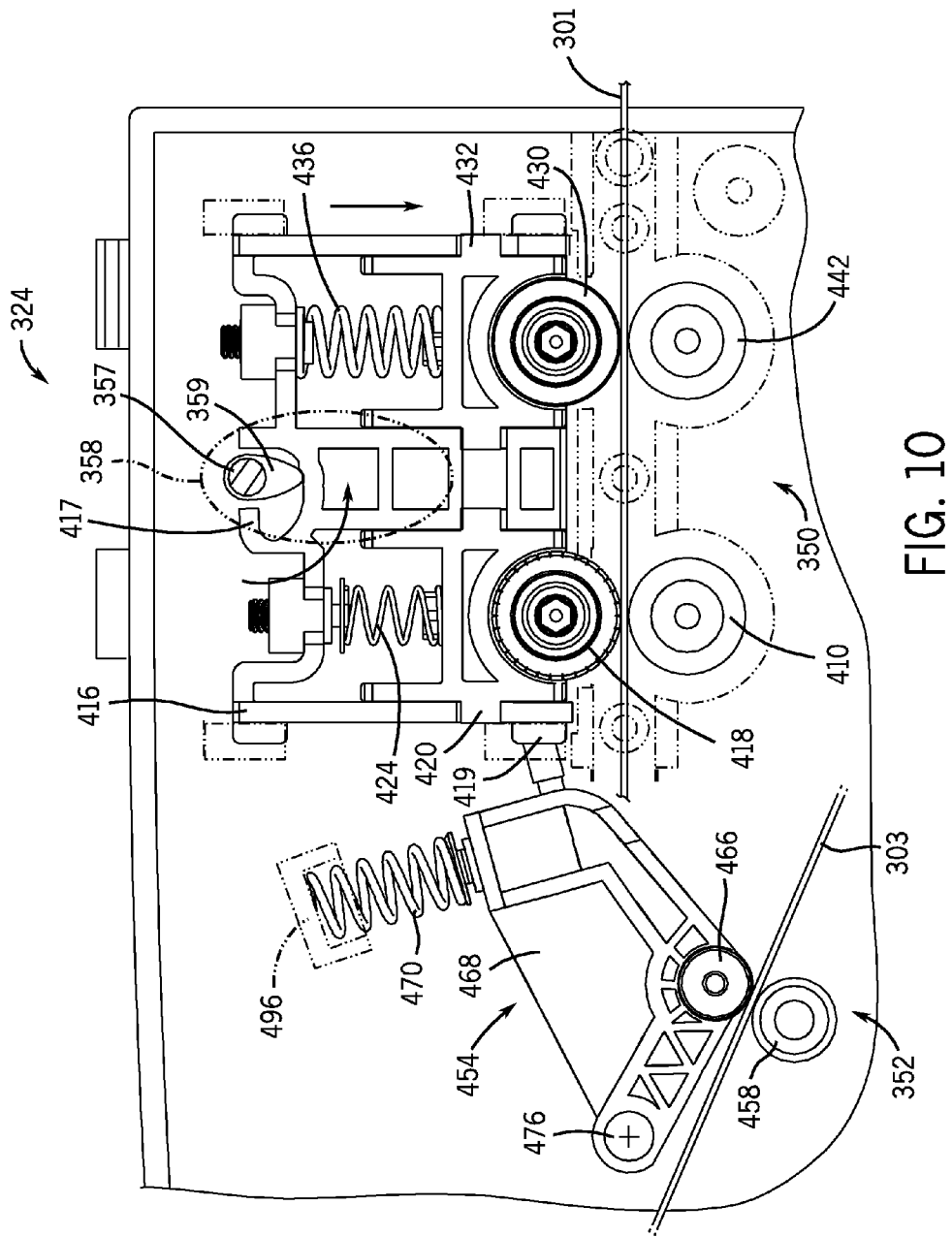
FIG. 10 is a top view showing the axial drive assembly in the "engaged" position.

FIG. 9 shows a top view of axial drive assembly 324 in the "loading" configuration with handle 358 (shown in broken lines) rotated such that handle 358 is generally parallel to guide wire channel 364. FIG. 10 shows a top view of axial drive assembly 324 in the "loaded" or "use" configuration with handle 358 rotated such that it is generally perpendicular to guide wire channel 364. Generally, when handle 358 is moved from the position of FIG. 10 to the position of FIG. 9, the engagement surfaces of both guide wire axial drive mechanism 350 and working catheter axial drive mechanism 352 are moved away from each other increasing the space between the pairs of wheels in the drive mechanisms. This provides sufficient space between the wheels of each drive mechanism to allow the user to place guide wire 301 and working catheter 303 into the channels between the wheels. Generally, as handle 358 is moved from the position of FIG. 9 to the position of FIG. 10, the engagement surfaces of both guide wire axial drive mechanism 350 and working catheter axial drive mechanism 352 are moved toward each other bringing the engagement surfaces of each drive mechanism into engagement with guide wire 301 or working catheter, respectively.

In the embodiment shown, handle 358 is coupled to a shaft 357. Shaft 357 includes a cam section 359 and housing 416 includes a cam surface 417. As handle 358 rotates from the position shown in FIG. 9 to the position shown in FIG. 10, cam section 359 of shaft 357 moves along cam surface 417 causing housing 416 to move toward guide wire 301. This motion engages guide wire 301 between drive wheel 410 and roller 418 and between roller 430 and roller 442. When handle 358 is brought into the position of FIG. 10, springs 424 and 436 are compressed to the proper tension to allow drive wheel 410 to move guide wire 301 axial along its longitudinal axis.

In addition, housing 416 includes a tab 419 that is coupled to linkage 468. Thus, linkage 468 rotates about post 478 when housing 416 is moved to the position shown in FIG. 9. This movement draws roller 466 away from working catheter drive wheel 458. When, housing 416 is moved to the position shown in FIG. 10, roller 466 is moved toward catheter drive wheel 458 such that the engagement surfaces of roller 466 and drive wheel 458 engage working catheter 303. In one embodiment, cassette 300 is configured to allow the user to move the axial drive assembly 324 between the "use" and "loading" positions via manipulation of controls at workstation 14. Cassette 300 may also be configured to allow the user to move the axial drive assembly 324 between the "use" and "loading" position manually.

Figure 11:
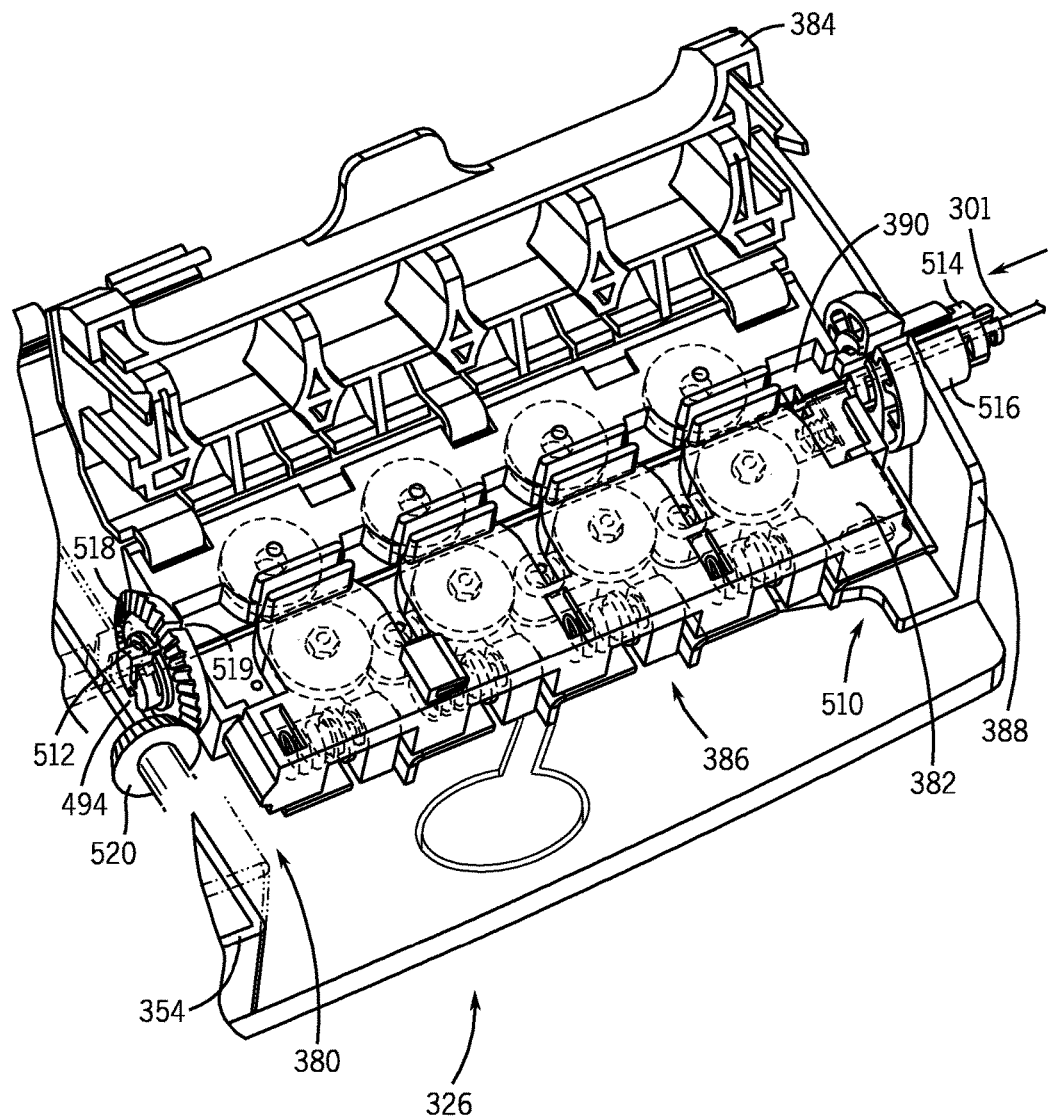
FIG. 11 is a top perspective view of a rotational drive assembly of a cassette showing the engagement structure in broken lines beneath the chassis.
Figure 12:
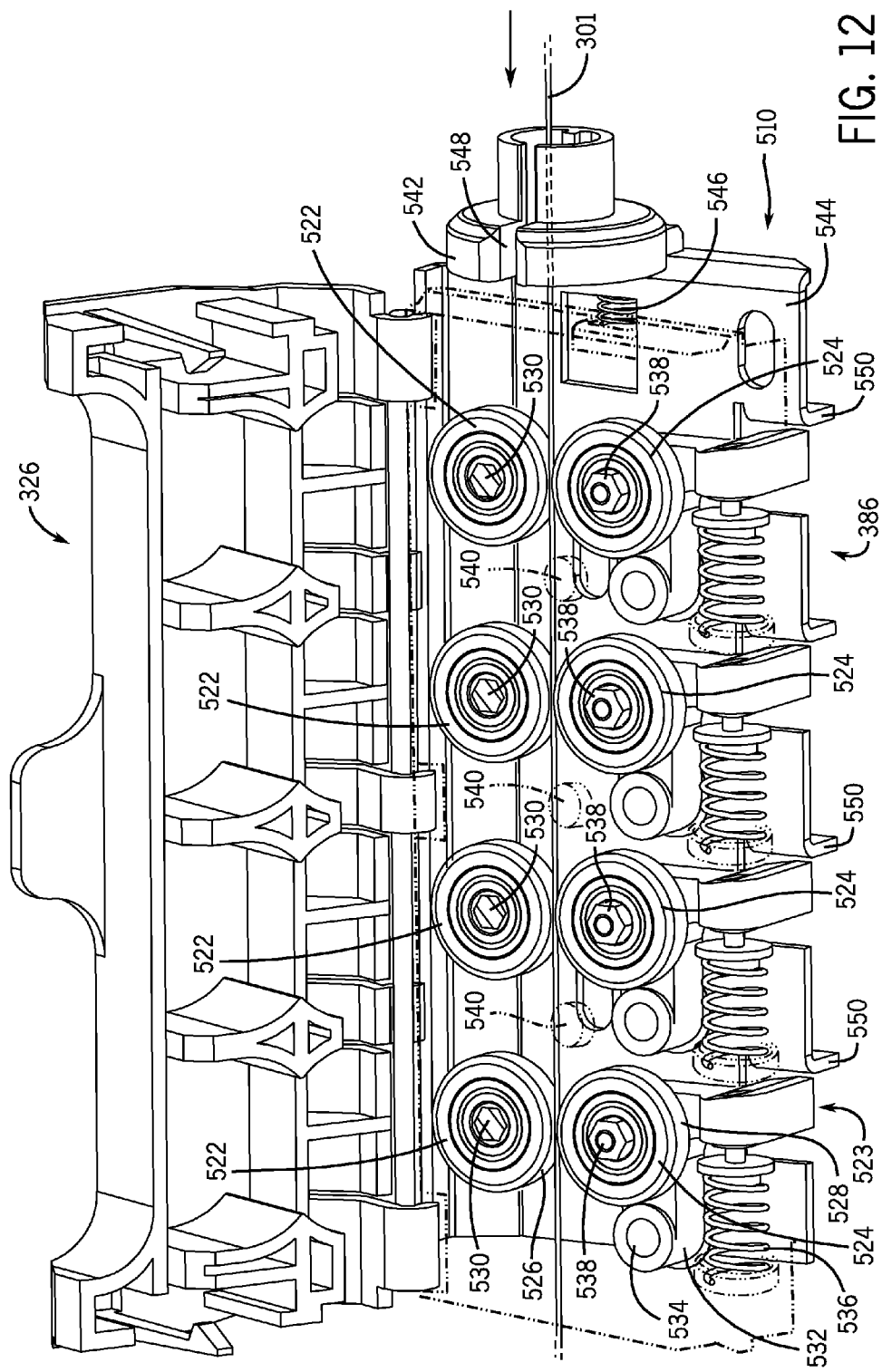
FIG. 12 is a top perspective view of a rotational drive assembly with the chassis shown in broken lines.

FIGS. 11 and 12 show a perspective view of rotational drive assembly 326 showing cover 384 in the open position. Rotational drive assembly 326 includes rotational drive mechanism 380, chassis 382, an engagement structure 386, and a disengagement assembly 510. Chassis 382 fits over engagement structure 386 and provides mounting for various components of rotational drive assembly 326. Chassis 382 includes a front shaft 512 and a rear shaft 514. As discussed above, front shaft 512 is rotatably received within collar 494 of top deck 354, and rear shaft 514 is rotatably received within collar 516 such that rotational drive mechanism 380 is able to rotate relative to journal 388. As shown, collar 516 extends through and is supported by journal 388 such that rear shaft 514 rotates within collar 516 as rotational drive mechanism 380 is rotated. Collar 516 rests within a recess or slot formed within journal 388. In another embodiment, rear shaft 514 may be in direct contact with journal 388 such that rear shaft 514 rotates within the recess or slot of journal 388 as rotational drive mechanism 380 is rotated. Guide wire channel 390 extends the length of chassis 382 through both front shaft 512 and rear shaft 514.

Rotational drive mechanism 380 includes rotation bevel gear 518 that engages a drive gear 520. Bevel gear 518 is rigidly coupled to front shaft 512 of chassis 382 such that rotation of bevel gear 518 rotates chassis 382. Drive gear 520 is coupled to a rotational actuator positioned in motor drive base 302 and engages bevel gear 518. Rotation of the rotational actuator in motor drive base 302 causes drive gear 520 to rotate which causes bevel gear 518 to rotate which in turn causes rotational drive mechanism 380 to rotate. Rotational drive mechanism 380 is allowed to rotate about the longitudinal axis of guide wire channel 390 via the rotatable connections between front shaft 512 and top deck 354 and between rear shaft 514 and journal 388. Bevel gear 518 further includes a slot 519 in axial alignment with guide wire channel 390. Slot 519 allows the user to place guide wire 301 into guide wire channel 390 by dropping it in vertically as opposed to threading it through bevel gear 518. In one embodiment, rotational drive assembly 326 is equipped with one or more sensors that are configured to measure an aspect (e.g., speed, position, acceleration, etc.) of rotation of the guide wire and/or any other structure of rotational drive assembly 326. The sensors that measure rotation of the guide wire may include magnetic encoders and/or optical sensors as discussed above regarding the sensors that measure axial motion of the guide wire and/or working catheter. However, any suitable sensor (e.g., resolvers, sychros, potentiometers, etc.) may be used to detect rotation of the guide wire.

Referring to FIG. 12, engagement structure 386 is shown according to an exemplary embodiment. As shown, engagement structure 386 includes four pairs of idler wheels or rollers. Each pair of rollers includes a fixed wheel 522 and an engagement wheel 524. Fixed wheels 522 are rotatably coupled to chassis 382 via fixation posts 530. Each engagement wheel 524 is part of an engagement wheel assembly 523. Each engagement wheel assembly 523 includes a pivoting body, shown as pivot yoke 532, and a spring 536. Each engagement wheel is mounted to pivot yoke 532 via a mounting post 538. Each pivot yoke 532 is pivotally coupled to chassis 382 via fixation posts 534.

Each fixed wheel 522 includes an outer or engagement surface 526 and each engagement wheel 524 includes an outer or engagement surface 528. Generally, FIG. 12 shows engagement structure 386 in the "use" or "engaged" position. In the "engaged" position, guide wire 301 is positioned between fixed wheels 522 and engagement wheels 524 such that engagement surfaces 526 and 528 are able to engage guide wire 301. In this embodiment, engagement surface 526 and engagement surface 528 of each pair of rollers define a pair of engagement surfaces. The force applied to guide wire 301 by engagement surfaces 526 and 528 is sufficient to cause the guide wire to rotate about its longitudinal axis as rotational drive assembly 326 is rotated. Further, the force applied to guide wire 301 by engagement surfaces 526 and 528 is also sufficient to allow the guide wire to be moved axially by guide wire axial drive mechanism 350. While FIG. 12 shows wheels 522 and 524 having substantially smooth outer engagement surfaces, in other embodiments, wheels 522 and 524 may include a textured engagement surface as shown in FIGS. 18, 19A and 19B, discussed in more detail below.

Springs 536 are biased to exert a force onto pivot yokes 532 causing each engagement wheel 524 to engage the opposite fixed wheel 522. The generally L-shape of pivot yoke 532 allows springs 536 to be aligned with the longitudinal axis of guide wire 301 and still cause engagement between engagement wheels 524, fixed wheels 522, and the guide wire. This allows the lateral dimension of rotational drive assembly 326 to be less than if springs 536 were positioned perpendicular to the longitudinal axis of the guide wire. Springs 536 are selected, tuned, and/or adjusted such that the proper amount of force is applied to the guide wire by engagement surfaces 526 and 528 in the "engaged" position.

Cassette 300 also includes a series of magnets 540 located beneath guide wire channel 390. Because, in at least some embodiments the guide wire is made from a magnetic material, magnets 540 are able to interact with the guide wire. In this embodiment, the magnetic attraction created by magnets 540 helps the user position guide wire 301 during loading by drawing guide wire 301 into guide wire channel 390. The magnetic attraction created by magnets 540 also tends to hold guide wire 301 within guide wire channel 390 during advancement and/or retraction of the guide wire. Further, magnets 540 help to hold guide wire 301 straight (i.e., parallel to the longitudinal axis of guide wire channel 390) to aid in the axial movement caused by guide wire axial drive mechanism 350.

Rotational drive assembly also includes a disengagement assembly 510. Disengagement assembly 510 includes a stepped collar 542, a base plate 544, and a spring 546. Stepped collar 542 is coupled to base plate 544, and spring 546 is coupled at one end to chassis 382 and at the other end to base plate 544. Stepped collar 542 includes a slot 548 in axial alignment with guide wire channel 390. Like slot 519, slot 548 allows the user to place guide wire 301 into guide wire channel 390 by dropping it in vertically as opposed to threading it through stepped collar 542. Base plate 544 includes a plurality of engagement arms 550 that extend generally perpendicular to the plane defined by base plate 544.

Figure 13:
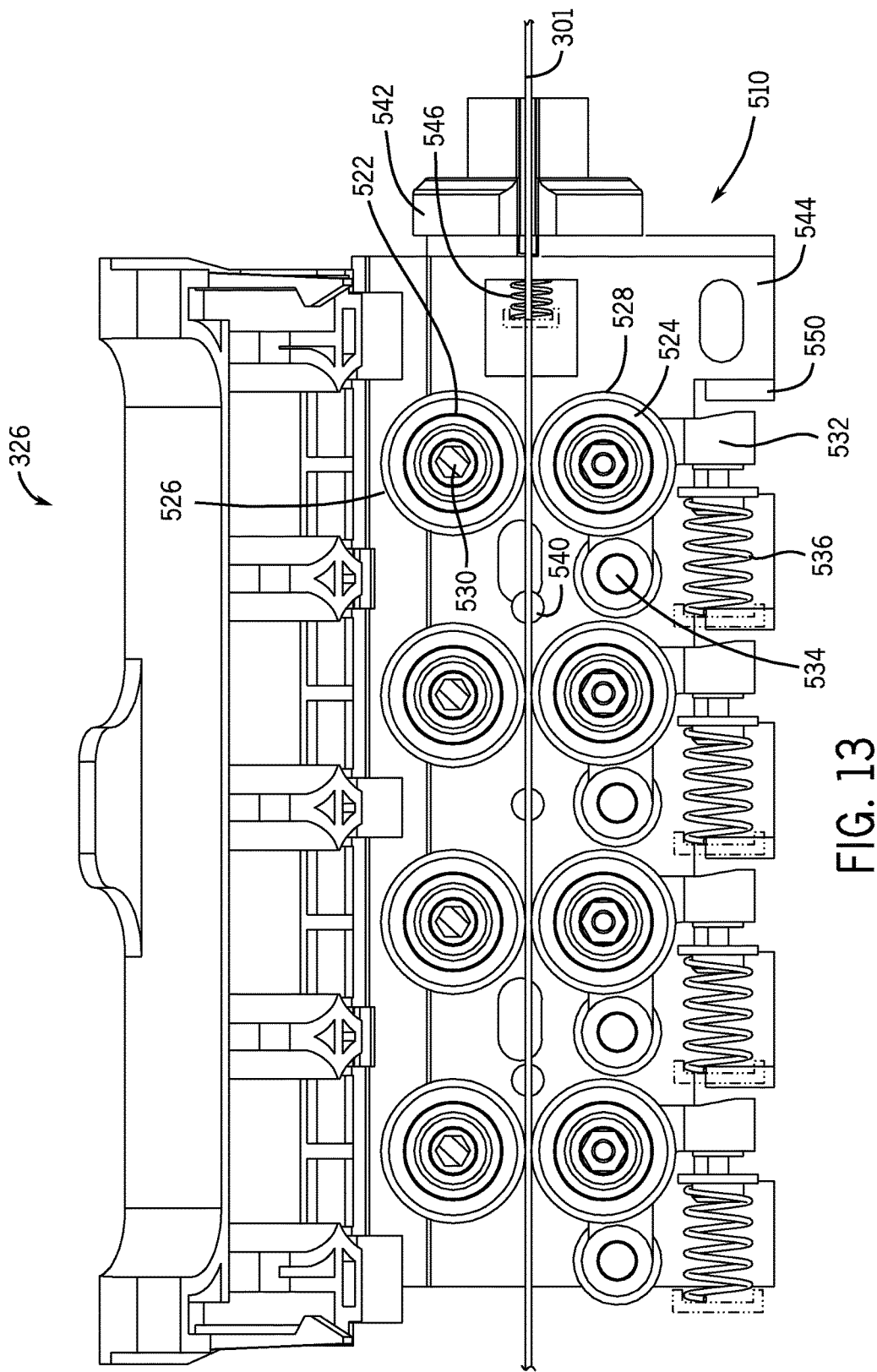
FIG. 13 is a top view of the rotational drive assembly in the "engaged" position.
Figure 14:
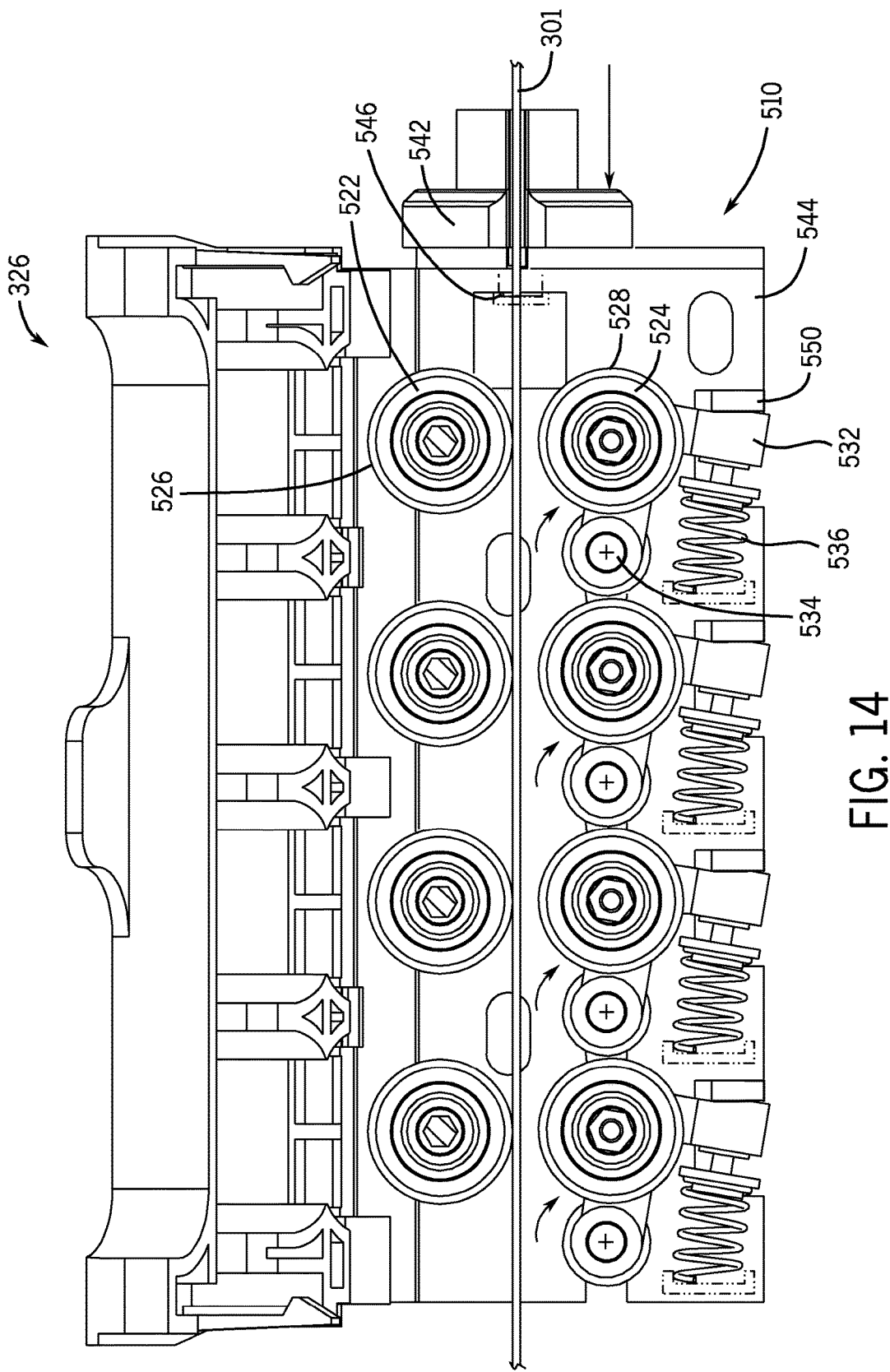
FIG. 14 is a top view of the rotational drive assembly in the "disengaged" position.

Generally, disengagement assembly 510 allows engagement wheels 524 to be moved away from fixed wheels 522. Referring to FIGS. 13 and 14, FIG. 14 shows a top view of rotational drive assembly 326 in the "loading" configuration, and FIG. 13 shows a top view of rotational drive assembly 326 in the "loaded" or "use" configuration. To cause engagement wheels 524 to disengage from guide wire 301, an axially directed force (depicted by the arrow in FIG. 14) is applied to stepped collar 542. This causes base plate 544 to move toward the front of cassette 300 in the direction of the arrow. As base plate 544 moves forward, spring 546 is compressed, and engagement arms 550 are brought into contact with pivot yokes 532. The contact between engagement arms 550 and pivot yokes 532 causes springs 536 to be compressed, and pivot yokes 532 pivot about fixation posts 534. As pivot yokes 532 pivot, engagement wheels 524 are drawn away from fixed wheels 522. As shown in FIG. 14, this provides sufficient space between engagement wheels 524 and fixed wheels 522 to allow the user to place guide wire 301 into guide wire channel 390.

When the axial force is removed from stepped collar 542, engagement wheels 524 move from the position shown in FIG. 14 to the "engaged" position shown in FIG. 13. When the axial force is removed, spring 546 and springs 536 are allowed to expand causing engagement arms 550 to disengage from pivot yokes 532. Pivot yokes 532 pivot counter-clockwise about fixation posts 534, bringing engagement wheels 524 back toward guide wire channel 390 causing engagement surfaces 526 of fixed wheels 522 and engagement surfaces 528 of engagement wheels 524 to engage guide wire 301.

In one embodiment, a user may activate controls located at workstation 14 to cause rotational drive assembly 326 to move between the "use" position and the "loading" position. In this embodiment, rotational drive assembly 326 is automatically rotated such that guide wire channel 390 is facing generally upward to allow for easy loading or removal of the guide wire. In the embodiment shown, chassis 382 rotates relative to stepped collar 542. In this embodiment, when rotational drive assembly 326 is in the "loading" position, a path defined by the engagement surfaces of engagement structure 386 and guide wire channel 390 align with slot 548 of stepped collar 542. Motor drive base 302 may also include a structure (e.g., two rods, etc.) that applies the axial force to stepped collar 542 in response to a user's activation of controls located at workstation 14. The structure applies the axial force to the stepped collar 542 to cause engagement structure 386 to disengage from the guide wire. Next, cover 384 is moved from the closed position to the open position allowing the user to access guide wire channel 390 to either remove or install the guide wire. In one embodiment, cassette 300 and/or motor drive base 302 includes motors or other actuators that cause the covers of cassette 300 to open in response to a user's activation of controls at workstation 14.

Figure 15:
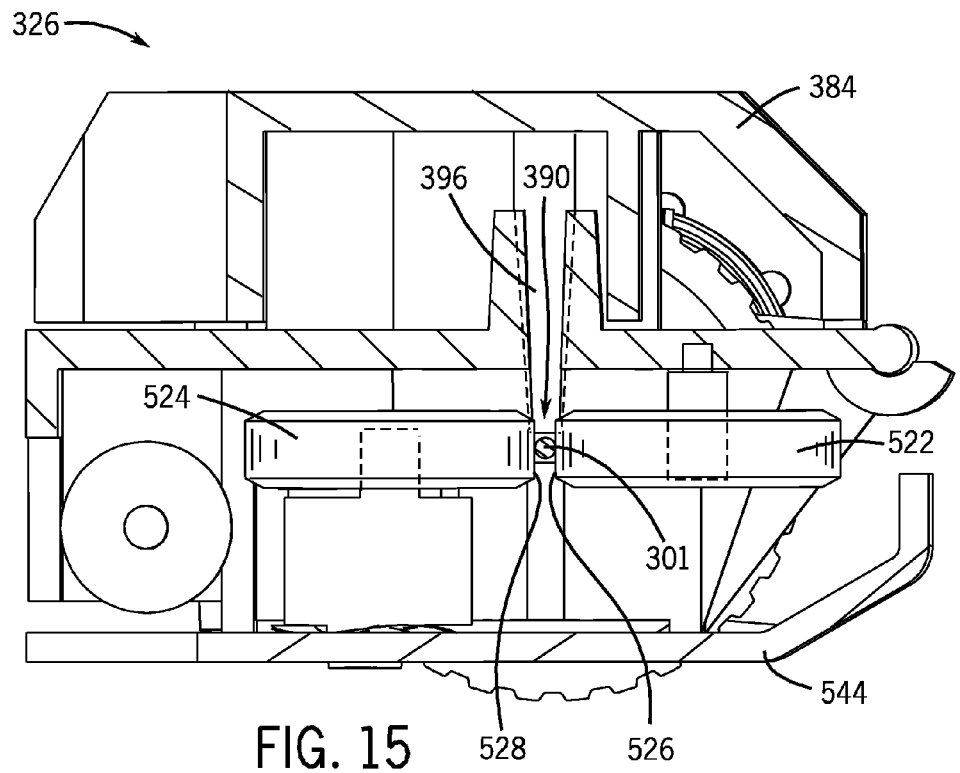
FIG. 15 is a sectional view of the rotational drive assembly taken generally along line 15-15 in FIG. 6.

FIG. 15 shows a cross-sectional view of rotational drive assembly 326 as indicated by the corresponding sectional line in FIG. 6. FIG. 15 depicts guide wire 301 within guide wire channel 390. As shown in FIG. 15, when cover 384 is in the closed position, tab 396 rests over guide wire channel 390. As shown in FIG. 15, tab 396 helps hold guide wire 301 in guide wire channel 390 by restricting movement of guide wire 301 in a direction perpendicular to the plane defined by base plate 544 (this direction of restriction is the vertical direction in the orientation of FIG. 15). Guide wire 301 is engaged on one side by engagement surface 526 of fixed wheel 522 and on the other side by engagement surface 528 of engagement wheel 524.

In a further embodiment a drive mechanism is provided which optimizes the manner in which axial and rotational motion is imparted to a robotic catheter device. In this regard, for ease of description the term catheter device is used in an expansive sense to encompass not only guide catheters and working catheters such as those used to deploy angioplasty balloons and stents but also the guide wires used in conjunction with the guide and working catheters regardless of the fact that guide wires are clearly not a type of catheter. This drive mechanism employs tires mounted on hubs as described above in Paragraph [0125] and also referred to as wheels to impart both axial and rotational motion to catheter devices (used in a sense analogous to percutaneous device and therefore encompassing guide wires) which optimize the simultaneous delivery of both types of motion. This optimization involves balancing the drive and resistance features of both the tires used to impart the axial motion and the tires used to impart rotational motion. Thus it is desirable that the tires imparting axial motion be efficient at doing so without creating undue resistance to rotational motion and that the tires imparting rotational motion be efficient at doing so without creating undue resistance to axial motion.

The drive mechanism includes a tire of a drive wheel and a tire of an idler wheel which interact with each other and the catheter device to cause it to move along its axis. Each of the tires has an engagement surface which interacts with a catheter device. These engagement surfaces are free of any gripping features which run perpendicular to the axis of the catheter device. This is in contrast to providing them with slits which do run perpendicular to the axis of the catheter device as described above in Paragraphs [0119-0121]. It is expected that such perpendicular features will impart resistance to rotational motion which out weights any benefit to imparting axial motion in a mechanism which optimizes the simultaneous impartation of both motions.

The drive mechanism also includes a set of tires which are part of wheels of a rotational drive assembly which cause the catheter device to rotate about its axis. These tires each have an engagement surface which interacts with the catheter device and which has a gripping feature which runs perpendicular to the axis of the catheter device. This feature enhances the ability of these tires to impart rotational motion to the catheter device without an objectionable increase in the resistance to axial motion in a mechanism which optimizes the simultaneous impartation of both motions.

A useful perpendicular gripping feature is a series of slits in the outside circumference of such a tire. In one embodiment these slits are of the type described below in Paragraphs [0119-0121]. One embodiment features these slits being present on the engagement surfaces of both of the tires.

One embodiment involves using tires on the rotational drive assembly wheels which are relatively soft compared to the range of harnesses available in polymer wheels. It is expected that the softer wheels will provide better rotational or torsional gripping of the catheter device when imparting rotational motion but will still offer low resistance to axial motion. In one embodiment the tires have a durometer hardness of less than about 85 A.

One embodiment involves having the tires of the rotational drive assembly wheels apply a substantially lighter pinch force to the catheter device than do the drive wheel tire and idler wheel tire. In one embodiment the drive wheel tire and the idler wheel tire apply a pinch force of about 9 pounds to the catheter device and the tires of rotational drive assembly wheels apply a pinch force of about 1.25 pounds to the catheter device. In this regard, the reference is to the pinch force applied by each set of rotational drive assembly tires as opposed to the aggregate pinch force of all the sets which may be part of the rotational drive assembly.

In one embodiment the rotational drive assembly has three sets of wheels and associated tires as opposed to the four illustrated in FIGS. 11-14 and 23. The number of sets is a function of the efficiency of each set in imparting rotational motion to the catheter device and thus as the efficiency of each set is improved, for instance by perpendicular slits, it may be possible to reduce the number of sets and still achieve acceptable performance.

In one embodiment the engagement surfaces of both the drive wheel tire and the idler wheel tire have a durometer hardness of at least about 95 A. It has been observed that when both engagement surfaces are relatively hard the efficiency of imparting axial motion is enhanced, particularly when the surface of the catheter device is wet. In use the outer surface of catheter devices, especially guide wires, may become covered with liquids which can affect their interactions with drive and idler tires and that this may be addressed by both having hard engagement surfaces.

In one embodiment the auxiliary encoder wheel tire and an encoder idler wheel tire which interacts with the auxiliary encoder wheel tire apply a substantially lighter pinch force to the catheter device than do the drive wheel tire and idler wheel tire. It is expected that the encoder assembly will be able to provide a reasonably precise measure of the axial motion of the catheter device while offering less resistance to axial motion with a lighter pinch force. In one embodiment the drive wheel tire and the idler wheel tire apply a pinch force of about 9 pounds to the catheter device and the auxiliary encoder wheel tire and an encoder idler wheel tire apply a pinch force of about 0.75 pounds to the catheter device.

In one embodiment the radial thickness of both the drive wheel tire and the idler wheel tire is reduced. It is expected that this will give performance equivalent to or better harder tires with greater radial thickness. In one embodiment the outside diameter of the tires is maintained constant so it is necessary to increase the outside radius of the hubs on which the two tires are mounted. In one embodiment the radial thickness of both the drive wheel tire and the idler wheel tire is between about 0.03 and 0.06 inches. The reduction of radial thickness allows a reduction in the hardness of the engagement surface of the tires and this, in turn, is expected to reduce the rolling resistance of the tires. In one embodiment the engagement surface of each the drive wheel tire and the idler wheel tire has a durometer hardness of less than about 50D.

In one embodiment the drive mechanism is involved in imparting axial and rotational motion to a guide wire, which in a broad sense can be thought of as a catheter device (It typically functions in conjunction with a guide catheter or a working catheter or both to accomplish a given medical procedure). The guide wire is the type of percutaneous device which is most typically subjected to the simultaneous application of both axial motion and rotational motion. In one embodiment the guide wire has a diameter between about 0.014 inches and 0.038 inches. The 0.014 inch diameter guide wire is commonly used in conjunction with a robotic catheter system.

In yet another alternative embodiment the drive mechanism makes use of composite tires on its various wheels. This allows a separation between the engagement surface properties and the overall resilience experienced by the catheter device, such as a guide wire, which is being driven. The drive mechanism has a drive wheel tire and an idler wheel tire which interact with each other, each of which has an engagement surface which interacts with a catheter device to cause it to move along its axis and a set of rotational drive assembly wheel tires, each of which has an engagement surface which interacts with a catheter device to cause it to rotate about its axis. One or more of the tires has a composite structure in which a material or structure of higher resilience is interposed between its engagement surface and the hub on which it is mounted. In one embodiment it is the rotational drive assembly wheel tires which have the composite structure. In one embodiment interposed material or structure of higher resilience is a pressurized fluid, a high resistance o-ring or a canted coil spring. If pressurized fluid, such as air, is to be used some structure will be needed to contain it but such structures be readily apparent to those of ordinary skill in the art. One approach is to provide the tires with side walls and to mount them to the hub in a manner analogous to that in mounting automotive tires to their wheels. Suitable canted springs are sold by BalSeal. It is expected that this composite tire approach would reduce the rolling resistance and, in the case of the rotational drive assembly wheel tires, this would be without a loss in the torsional engagement.

Figure 16:
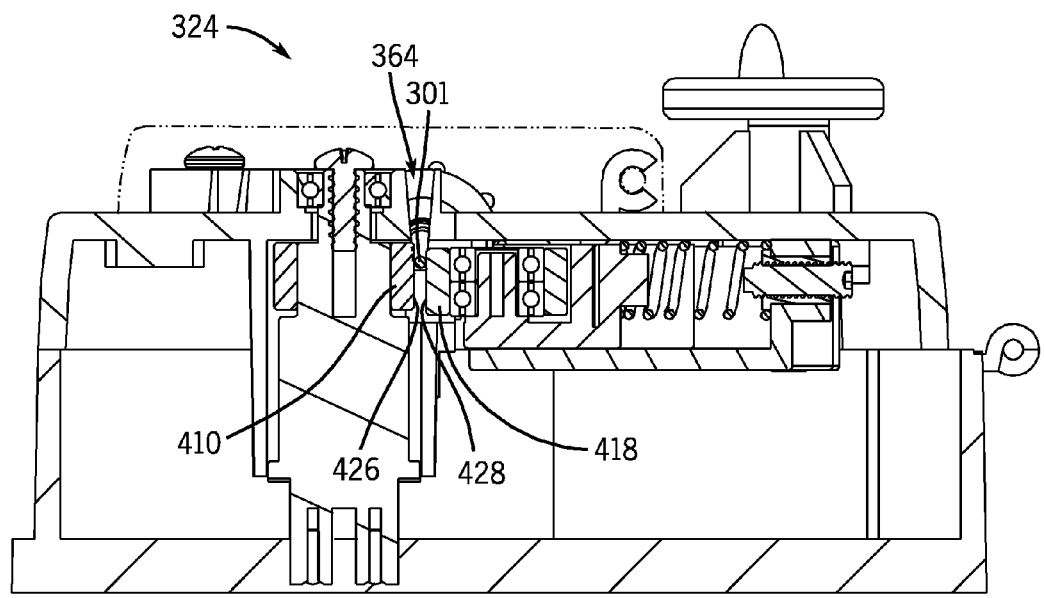
FIG. 16 is a sectional view of the axial drive assembly taken generally along line 16-16 in FIG. 6.

FIG. 16 shows a cross-sectional view of axial drive assembly 324 as indicated by the corresponding sectional line in FIG. 6. FIG. 16 depicts guide wire 301 within channel 364. Guide wire 301 is engaged on one side by engagement surface 426 of drive wheel 410 and on the other side by engagement surface 428 of roller 418.

Figure 17C:
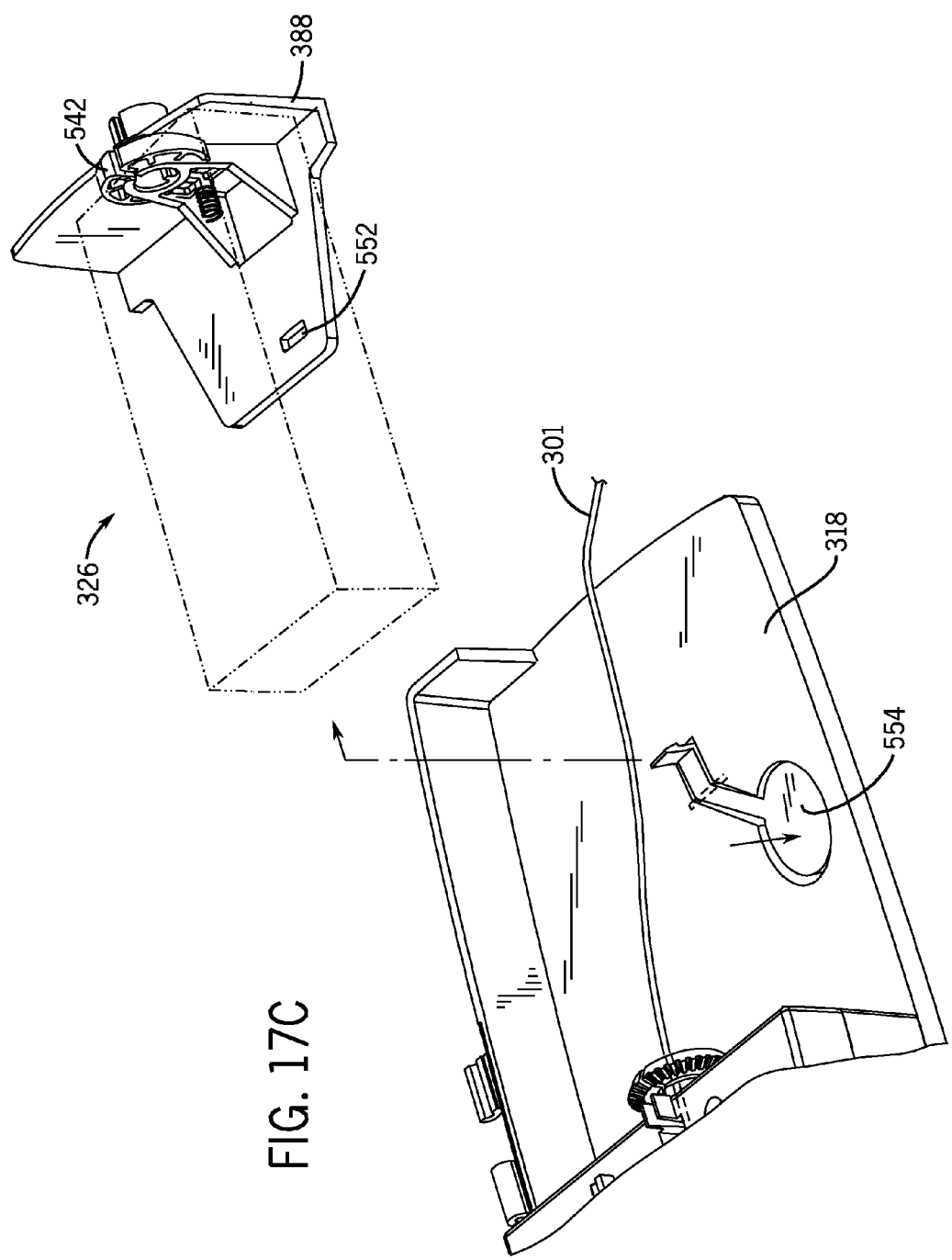
FIG. 17C shows removal of the rotational drive assembly from the base plate of the cassette leaving the guide wire in place.

Under certain circumstances, it may be desirable to disconnect rotational drive assembly 326 from cassette 300. Referring to FIGS. 17A-17C, cassette 300 may be configured to allow rotational drive assembly 326 (shown schematically by broken lines in FIGS. 17A-17C) to be disconnected from cassette 300. In one such embodiment, cassette 300 includes journal 388, and rotational drive mechanism 380 is rotatably coupled to journal 388. In this embodiment, journal 388 is releasably coupled to housing 316 such that both journal 388 and rotational drive mechanism 380 may be removed from housing 316 without removing the guide wire from the patient and/or without removing cassette 300 from base 302. In one such embodiment, following release of journal 388 from housing 316, the user may remove (e.g., pull, slide, etc.) both journal 388 and rotational drive mechanism 380 over the proximal end of the guide wire.

In one embodiment, journal 388 includes a slot 552, and base plate 318 includes a release button 554. Release button 554 is coupled to ramp 556, and ramp 556 includes wedge-shaped end 558. As shown in FIG. 17A, wedge-shaped end 558 passes through slot 552 to couple journal 388 to base plate 318. When a downward force is applied to release button 554, wedge-shaped end 558 is allowed to disengage from slot 552 allowing rotational drive assembly 326 and journal 388 to disconnect from base plate 318.

Next, rotational drive assembly 326 is disengaged from guide wire 301. As discussed above, regarding FIGS. 13 and 14, by applying an axial force to stepped collar 542, engagement structure 386 disengages from the guide wire. Once engagement structure 386 is disengaged from guide wire 301, the rotational drive assembly 326 may be moved over the proximal end of the guide wire while the guide wire slides freely though guide wire channel 390. Removal of rotational drive assembly 326 from cassette 300 may be necessary if, for example, bedside system 12 loses power preventing motor drive base 302 from placing rotational drive assembly into the "loading" configuration. In this case, removal of rotational drive assembly 326 allows the user to either remove the guide wire and working catheter from the patient manually or to complete the procedure manually.

Referring to FIGS. 18, 19A and 19B, a wheel (e.g., drive wheel 410) for a drive mechanism of a robotic catheter system is shown according to an exemplary embodiment. As shown in FIGS. 18, 19A and 19B, engagement surface 426 of drive wheel 410 is configured to increase the ability of the wheel to grip and to impart axial motion to the guide wire. Engagement surface 426 of drive wheel 410 is textured (e.g., non-smooth, treaded, slotted, slitted, etc.) to increase friction between the wheel and the guide wire. In particular, in the embodiment shown, drive wheel 410 includes a plurality of slits 600 formed in the outer layer of the material of drive wheel 410. Slits 600 act to provide better grip between the wheel and the guide wire which provides for improved transmission of motion from the wheel to the guide wire and also decreases the chance that slippage will occur between the drive wheel and the guide wire. While the description of FIGS. 18-19B relates to drive wheel 410, it should be understood that any wheel of cassette 300 can be configured as discussed in relation to drive wheel 410. Accordingly, wheels 522 and 524 of rotational drive assembly 326 may have an engagement surface that is textured as described with wheels 410 and 418. Such that only one or both of wheels 522 and 524 may textured, or that only certain of wheels 522 are textured and/or only certain of wheels 524 are textured or only some combination of some but not all of wheels 522 and 524 are textured. It is also contemplated that some of the wheels 522 and 524 may be textured but with different tread configurations or with a different engagement surface material than other wheels 522 and 524. Applying a different engagement surface characteristic to different wheels may provide greater overall gripping, drive and rotational performance for the system under certain operating conditions. Further as noted, the texture of certain wheels 522 and 524 may be the same or different than the texture wheels 410 and 418 depending on the gripping, rotational and drive performance desired. The specific desired arrangement of engagement surfaces of the wheels may depend on the type of guide wire or working catheter or catheter that is being manipulated by the system as well as the type of procedure being employed on the patient.

As shown in FIG. 18, each slit 600 has substantially the same size, shape, etc., as the other slits 600. However, in other embodiments, slits 600 may having varying sizes, shapes, etc. In the embodiment shown, slits 600 are substantially linear and are positioned substantially parallel to the central axis (e.g., the axis of rotation) of drive wheel 410. Slits 600 extend the entire axial dimension of engagement surface 426, and, in this arrangement, slits 600 are substantially parallel to each other. In other embodiments, slits 600 may be other shapes or positioned in other configurations relative to engagement surface 426. For example, slits 600 may be curved having a component that extends in the circumferential direction along engagement surface 426. In other embodiments, slits 600 may have multiple segments positioned at angles relative to each other (e.g., a zigzag pattern).

Referring to FIGS. 19A and 19B, a top view of drive wheel 410 is shown. Slits 600 of drive wheel 410 are spaced at even intervals around drive wheel 410 and are substantially symmetric about the radial centerline of the slit. In various embodiments, the angle A between the radial centerlines of adjacent slits 600 may be selected to vary the gripping characteristic of the wheel. In various exemplary embodiments, the angle A between radial centerlines of adjacent slits 600 may be between about 5 degrees and about 20 degrees, specifically between about 10 degrees and about 15 degrees, and more specifically between about 11 degrees and 13 degrees. In the exemplary embodiment shown in FIGS. 18-19B, drive wheel 410 includes 30 slits 600 evenly spaced such that angle A is about 12 degrees.

The depth of slits 600 below the outer surface 426, shown as dimension D in FIG. 19B, may be selected to vary the gripping characteristics of wheel 410. In various embodiments, the depth of slits 600 may be selected to be between about 1 percent and about 10 percent of the diameter of wheel 410, specifically between about 1 percent and about 7 percent of the diameter of wheel 410, and more specifically between about 1.5 percent and about 6.4 percent of the diameter of wheel 410. In a specific embodiment, the diameter of wheel 410 is about 0.63 inches, and the depth D of slits 600 is between about 0.01 inches and about 0.04 inches.

The circumferential dimension of slits 600, shown as dimension W in FIG. 19B, may be selected to vary the gripping characteristics of wheel 410. In various embodiments, the circumferential dimension W of slits 600 may be selected to be between about 0 percent and about 10 percent of the circumference of wheel 410, specifically between about 0 percent and about 3 percent of the circumference of wheel 410, and more specifically between about 0 percent and about 1 percent of the circumference of wheel 410.

Further, the material of drive wheel 410 may be selected to vary the gripping characteristics of wheel 410. In one embodiment, drive wheel 410 may be made from a polymer material. In one embodiment, drive wheel 410 may be made from a thermoplastic polyurethane elastomer. In one specific embodiment, drive wheel 410 may be made from Texin RxT85A manufactured by Bayer MaterialScience.

In various embodiments, the hardness of the material of drive wheel 410 may be selected to vary the gripping characteristics of wheel 410. In various embodiments, the shore hardness of the material of drive wheel 410 is between about 10 A and about 100 A, specifically between about 50 A and about 100 A, and more specifically between about 75 A and about 95 A. In one specific embodiment, drive wheel 410 is made from a material having a shore hardness of about 85 A.

In one embodiment, drive wheel 410 may be formed from a molded piece of polymer material having a smooth outer surface. Drive wheel 410 may then be coupled to a hub 602 of a cylindrical pin or shaft. Following attachment to hub 602, slits 600 are created in the outer surface of drive wheel 410 using a cutting or slitting tool to produce slits 600 of the desired size, shape and positioning.

Drive wheel 410 may be attached to the hub in a variety of ways. In various embodiments, drive wheel 410 is coupled to hub 602 such that rotation of the shaft is transmitted to drive wheel 410 without slippage occurring between drive wheel 410 and hub 602. In one embodiment, drive wheel 410 is shaped as a ring having a central opening, and drive wheel 410 is mounted to hub 602 by stretching the material of drive wheel 410 and placing drive wheel 410 over hub 602 such that hub 602 is received in the central opening of drive wheel 410. In this embodiment, the elasticity of the material of drive wheel 410 is sufficient to firmly attach drive wheel 410 to hub 602 and to prevent movement of drive wheel 410 relative to hub 602 during rotation.

In other embodiments, drive wheel 410 may be attached to hub 602 by other means. In one embodiment, drive wheel 410 may be welded or bonded to hub 602, and, in another embodiment, drive wheel 410 may be attached to hub 602 using an adhesive. In yet another embodiment, drive wheel 410 may be coupled to hub 602 using mechanical attachment elements. For example, the outer circumferential surface of hub 602 may be formed with a series of posts, and the inner surface of drive wheel 410 may be formed with a series of recesses that receive the posts of hub 602.

Referring to FIGS. 20-23, a structure or clip, shown as wheel separator clip 610, is depicted according to an exemplary embodiment. Separator clip 610 is configured to engage rotational drive assembly 326 in a manner that causes each pair of wheels 522 and 524 to be held in the disengaged, "loading" position shown in FIG. 14. As noted above, in some embodiments, wheels 522 and 524 of rotational drive assembly 326 may be made from a deformable, polymer material. Further, because springs 536 act to bias wheels 522 and 524 to the engaged position shown in FIG. 13, when cassette 300 is not in use, wheels 522 and 524 will tend to assume the engaged position in which the outer surfaces of each wheel are in contact with each other. If cassette 300 is not used for a substantial period of time (e.g., during storage following manufacture, during storage between procedures, etc.), the constant contact between wheels 522 and 524 under the influence of springs 536 may cause deformation of wheels 522 and 524. For example, flattened sections may be formed along the outer surface of wheels 522 and 524 at the location of the contact between the wheels. Separator clip 610 may be used to engage rotational drive assembly 326 to resist the biasing force of springs 536 in order to hold wheels 522 and 524 in the "disengaged" position when cassette 300 is not in use. In this manner, separator clip 610 acts to prevent the deformation that wheels 522 and 524 may be susceptible to if the they are allowed to remain in the engaged position for an extended period of time.

Figure 20:
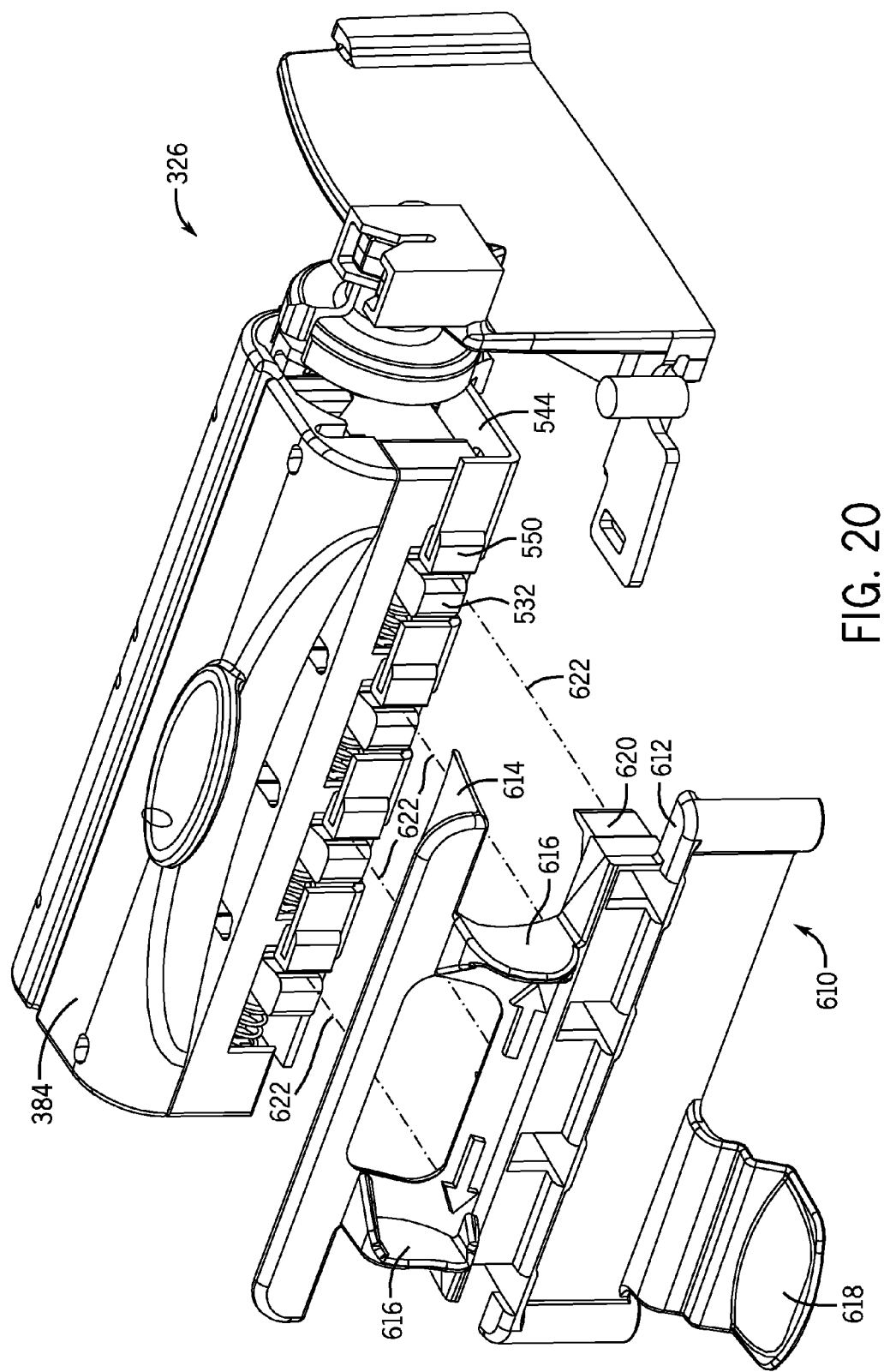
FIG. 20 is an exploded view showing a wheel separator structure according to an exemplary embodiment.
Figure 21:
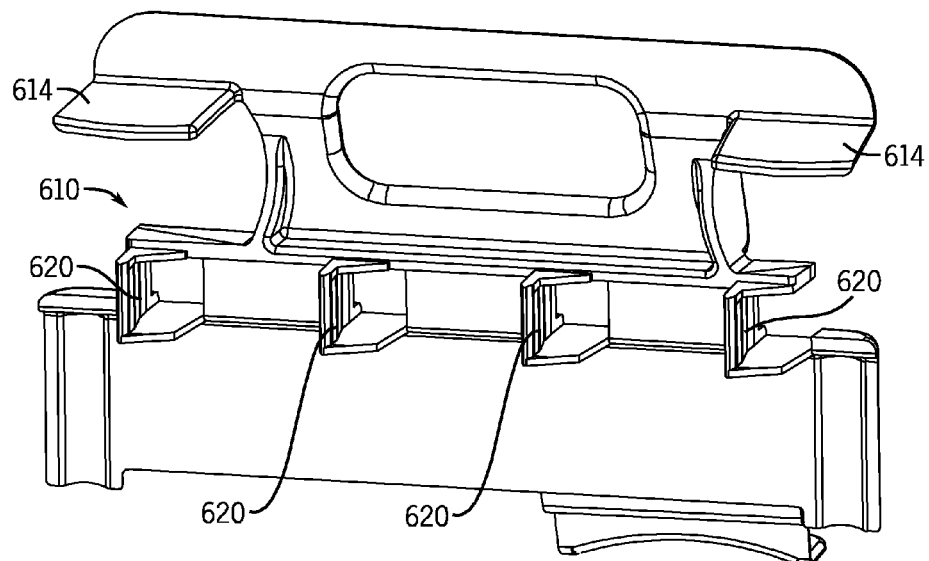
FIG. 21 is a rear perspective view of the structure of FIG. 20.

Referring to FIG. 20, an exploded view of separator clip 610 and rotational drive assembly 326 is shown. Separator clip 610 includes a body 612, a pair of upper walls 614 positioned substantially perpendicular to and extending from body 612, a pair of gripping surfaces 616, and a handle tab 618. Separator clip 610 also includes at least one arm 620 positioned to and extending from body 612. In an exemplary embodiment, separator clip 610 includes one arm 620 for each pair of wheels 522 and 524 in rotational drive assembly 326, and in the particular embodiment shown in FIG. 21, separator clip 610 includes four arms 620 corresponding to the four pairs of wheels 522 and 524 of rotational drive assembly 326.

Figure 22:
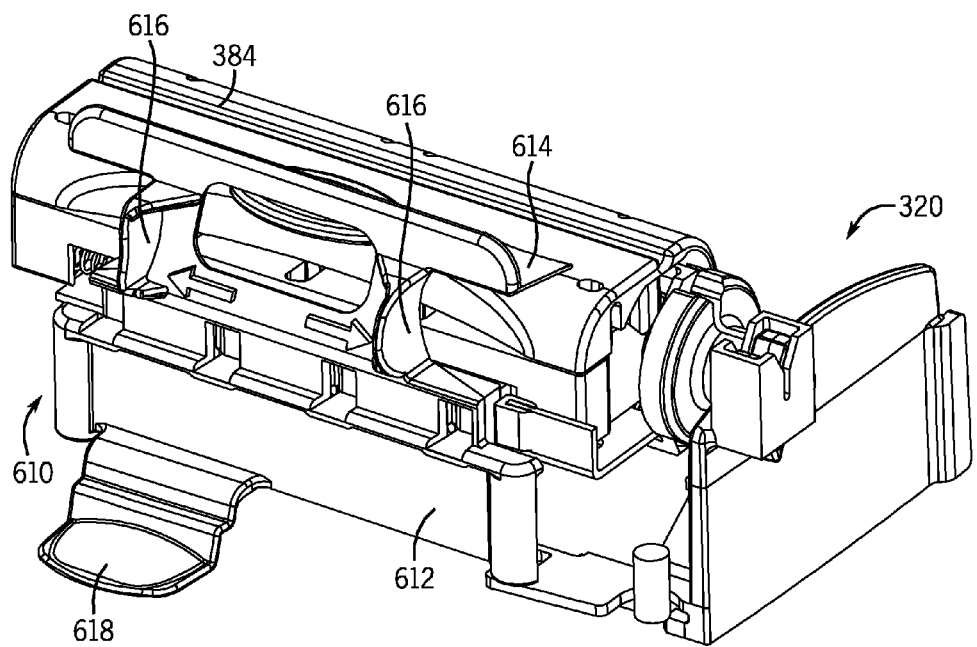
FIG. 22 is a front perspective view of the structure of FIG. 20 engaged with a rotational drive assembly according to an exemplary embodiment.

Separator clip 610 is shown engaged to rotational drive assembly 326 in FIG. 22, and the dotted lines 622 in FIG. 20 indicate the position of engagement between arms 620 of separator clip 610 and rotational drive assembly 326 when separator clip 610 is coupled to the rotational drive assembly. As indicated in FIG. 20, arms 620 of separator clip 610 are positioned between engagement arms 550 of base plate 544 and pivot yokes 532 of each wheel assembly 523 of rotational drive assembly 326. When separator clip 610 is engaged with rotational drive assembly 326, upper walls 614 are positioned in contact with the upper outer surface of cover 384 of rotational drive assembly 326. To hold and manipulate separator clip 610, the user may grasp gripping surfaces 616 and/or handle tab 618.

Figure 23:
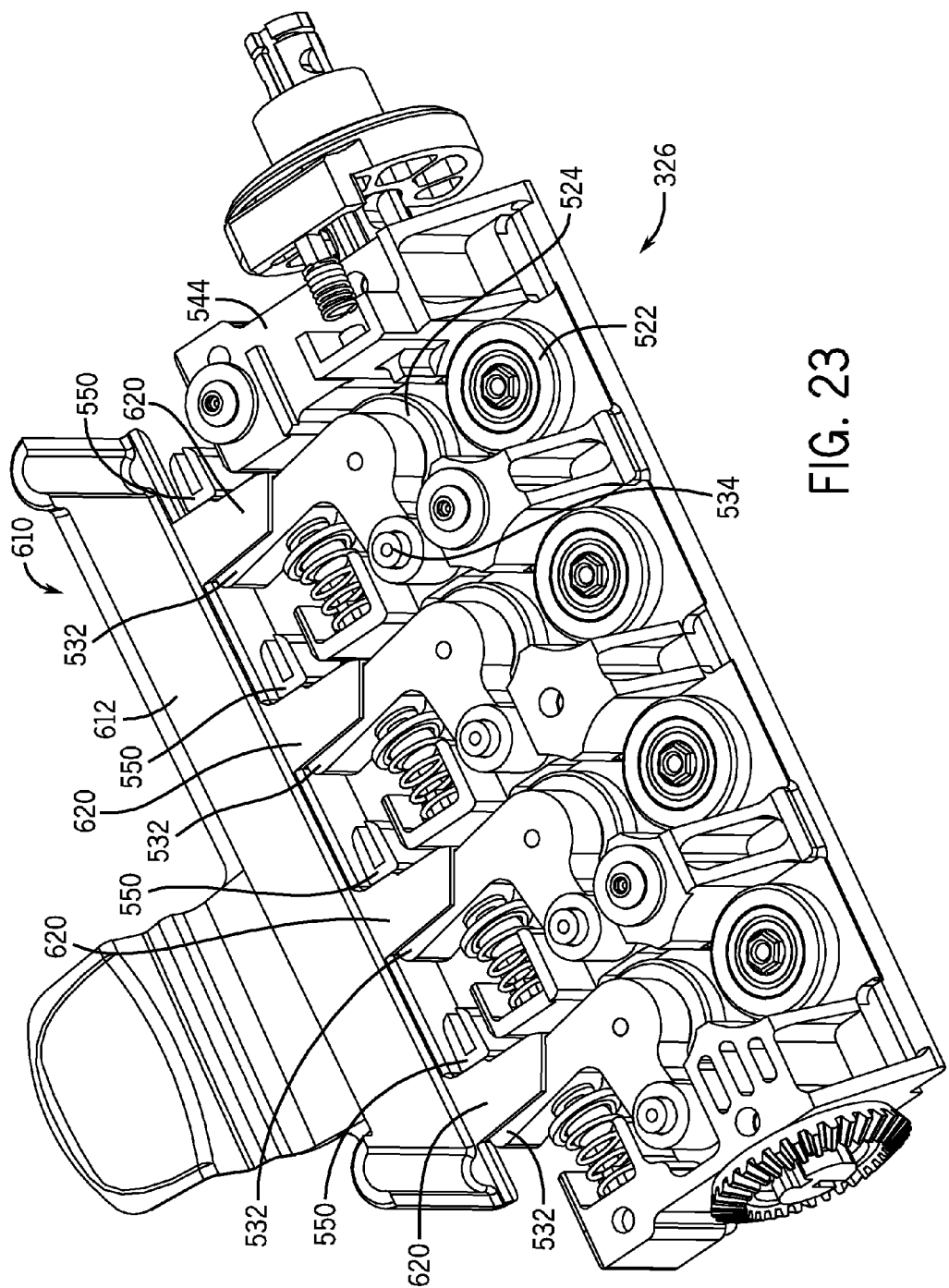
FIG. 23 is a perspective view from below of the structure of FIG. 20 engaged with a rotational drive assembly according to an exemplary embodiment.

Referring to FIG. 23, a bottom view of rotational drive assembly 326 is shown with separator clip 610 coupled to rotational drive assembly 326. Each arm 620 of separator clip 610 is positioned between one engagement arm 550 of base plate 544 and the opposing pivot yoke 532. In this position, each arm 620 includes a first surface, shown as the right-facing surface in FIG. 23, that is in contact with engagement arm 550 and a second surface, shows as the left-facing surface in FIG. 23, that is in contact with pivot yoke 532. The contact of the opposing surfaces of each arm 620 with engagement arms 500 and pivot yokes 532 causes each spring 536 to be compressed. The compression of springs 536 in turn causes each pivot yoke 532 to pivot about fixation post 534. As explained in detail above regarding FIGS. 13 and 14, compression of springs 536 and the resulting pivoting of each pivot yoke 532 moves each wheel 524 away from the opposing wheel 522. With separator clip 610 engaged between engagement arms 550 and pivot yokes 532, rotational drive assembly 326 is held in the disengaged position such that wheels 522 and 524 are not in contact with each other. In this manner, separator clip 610 acts to prevent deformation of wheels 522 and 524 that may otherwise be caused by constant, long-term contact between wheels 522 and 524. Prior to use of cassette 300, separator clip 610 is disengaged from rotational drive assembly 326 allowing wheels 522 and 524 to move into engagement under the force of springs 536.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A drive mechanism for a robotic catheter system, the drive mechanism being configured to impart both axial and rotational motion to a catheter device and comprising:
    a tire of a drive wheel and a tire of an idler wheel which interact with each other, each of which has an engagement surface which is configured to interact with a catheter device to cause it to move along its longitudinal axis and which is free of any slits that each have a centerline configured to run perpendicularly to the longitudinal axis of the catheter device; and
    a set of rotational drive assembly wheel tires each of which has an engagement surface which is configured to interact with the catheter device to cause it to rotate about its longitudinal axis and which have slits each having a centerline configured to run perpendicularly to the longitudinal axis of the catheter device.

2. The drive mechanism of claim 1 wherein the engagement surfaces of both of the rotational drive assembly wheel tires has a durometer hardness of no more than about 85 A.

3. The drive mechanism of claim 1 wherein the rotational drive assembly wheel tires of the set apply a substantially lighter pinch force to the catheter device than do the drive wheel tire and idler wheel tire.

4. The drive mechanism of claim 3 wherein the drive wheel tire and the idler wheel tire apply a pinch force of about 9 pounds to the catheter device and the rotational drive assembly wheel tires apply a pinch force of about 1.25 pounds to the catheter device.

5. The drive mechanism of claim 1 wherein there are three sets of rotational drive assembly wheel tires.

6. The drive mechanism of claim 1 wherein the engagement surfaces of both the drive wheel tire and the idler wheel tire have a durometer hardness of at least about 95 A.

7. The drive mechanism of claim 1 which includes an auxiliary encoder wheel tire with an engagement surface which interacts with the catheter device which has a durometer hardness of no more than about 85 A.

8. The drive mechanism of claim 7 wherein the auxiliary encoder wheel tire and an encoder idler wheel tire which interacts with the auxiliary encoder wheel tire apply a substantially lighter pinch force to the catheter device than do the drive wheel tire and idler wheel tire.

9. The drive mechanism of claim 8 wherein the drive wheel tire and the idler wheel tire apply a pinch force of about 9 pounds to the catheter device and the auxiliary encoder wheel tire and an encoder idler wheel tire apply a pinch force of about 0.75 pounds to the catheter device.

10. The drive mechanism of claim 8 wherein the engagement surface of each the drive wheel tire and the idler wheel tire has a durometer hardness of less than about 50D.

11. The drive mechanism of claim 1 wherein the radial thickness of both the drive wheel tire and the idler wheel tire is between about 0.03 and 0.06 inches.

12. The drive mechanism of claim 1 wherein catheter device is a guide catheter or a working catheter which deploys an angioplasty balloon or a stent.

13. The drive mechanism of claim 1 wherein the catheter device is a guide wire.

14. The drive mechanism of claim 13 wherein the guide wire has a diameter between about 0.014 inches and 0.038 inches.

15. The drive mechanism of claim 1 wherein the guide wire has a diameter of about 0.014 inches.

16. A drive mechanism for a robotic catheter system, the drive mechanism being configured to impart both axial and rotational motion to a catheter device and comprising:
    a drive wheel tire and an idler wheel tire which interact with each other, each of which has an engagement surface which is configured to interact with the catheter device to cause it to move along its longitudinal axis; and
    a set of rotational drive assembly wheel tires each of which has an engagement surface which is configured to interact with the catheter device to cause it to rotate about its longitudinal axis;
    wherein one or more of the tires has a composite structure in which a material or structure of higher resilience is interposed between its engagement surface and a hub on which it is mounted.

17. The drive mechanism of claim 16 wherein the rotational drive assembly wheel tires have the composite structure.

18. The drive mechanism of claim 17 wherein interposed material or structure of higher resilience is a pressurized fluid, a high resistance o-ring or a canted coil spring.

19. The drive mechanism of claim 16 wherein the engagement surface of at least one of the rotational drive assembly wheel tires has slits each having a centerline configured to run perpendicularly to the longitudinal axis of the catheter device.

20. The drive mechanism of claim 16 wherein the catheter device is a guide wire.

\* \* \* \* \*